(12) United States Patent
Nonogaki

(10) Patent No.: US 8,289,016 B2
(45) Date of Patent: Oct. 16, 2012

(54) EDDY-CURRENT FLAW DETECTION METHOD AND APPARATUS

(76) Inventor: Keiichi Nonogaki, Okazaki (JP)

( * ) Notice: Subject to any disclaimer, the term of this patent is extended or adjusted under 35 U.S.C. 154(b) by 425 days.

(21) Appl. No.: 12/672,078

(22) PCT Filed: May 1, 2008

(86) PCT No.: PCT/JP2008/058361
§ 371 (c)(1),
(2), (4) Date: Feb. 4, 2010

(87) PCT Pub. No.: WO2009/025105
PCT Pub. Date: Feb. 26, 2009

(65) Prior Publication Data
US 2011/0068783 A1    Mar. 24, 2011

(30) Foreign Application Priority Data

Aug. 21, 2007 (JP) ................. 2007-214494

(51) Int. Cl.
*G01R 33/12* (2006.01)
*G01N 27/84* (2006.01)
(52) U.S. Cl. ........................ 324/216; 324/240
(58) Field of Classification Search .................. 324/456, 324/216, 217, 237, 238, 240, 718
See application file for complete search history.

(56) References Cited

U.S. PATENT DOCUMENTS

| 5,006,800 | A  | 4/1991 | Hedengren et al. |
| 5,942,893 | A  | 8/1999 | Terpay |
| 6,344,739 | B1 | 2/2002 | Hardy et al. |
| 7,154,265 | B2 * | 12/2006 | Togo et al. ............ 324/239 |
| 2002/0079889 | A1 | 6/2002 | Givens et al. |
| 2006/0170420 | A1 | 8/2006 | Nishimizu et al. |

FOREIGN PATENT DOCUMENTS

| EP | 1217370 | 6/2002 |
| GB | 631987 | 11/1949 |
| JP | 3-167470 | 7/1991 |

(Continued)

OTHER PUBLICATIONS

Extended Search Report, mailed Jul. 19, 2012, from European Patent Office (E.P.O.) for corresponding European patent application.

*Primary Examiner* — Patrick Assouad
*Assistant Examiner* — Alesa Allgood
(74) *Attorney, Agent, or Firm* — Greenblum & Bernstein, P.L.C.

(57) ABSTRACT

A method of eddy-current flaw detexction where an exciting device and a receiving device are held in the vicinity of a conductor. An eddy current is generated in the conductor by a primary magnetic field generated by excitation, thereby generating a secondary magnetic field, wherein the state of the magnetic field is detected by the receiving device. The exciting device includes a coil and an iron core. The coil has a first current line and a second current line in which electric current flows in opposite directions. The iron core is gate-shaped in cross section and includes a first leg portion, a second leg portion, and a beam portion. The receiving device is disposed in a corner between the second leg portion and the conductor, on a side opposite the second current line on the outer side of the iron core.

18 Claims, 13 Drawing Sheets

FOREIGN PATENT DOCUMENTS

| | | |
|---|---|---|
| JP | 5-52816 | 3/1993 |
| JP | 10-73570 | 3/1998 |
| JP | 10-288606 | 10/1998 |
| JP | 10-307124 | 11/1998 |
| JP | 2000-131287 | 5/2000 |
| JP | 2000-227420 | 8/2000 |
| JP | 2000-235020 | 8/2000 |
| JP | 2003-149209 | 5/2003 |
| JP | 2003-344362 | 12/2003 |
| JP | 2006-194661 | 7/2006 |

* cited by examiner

EDDY-CURRENT FLAW DETECTION METHOD AND APPARATUS

TECHNICAL FIELD

The present invention relates to a technique of detecting a flaw by generating an eddy current.

BACKGROUND ART

When detection of a flaw such as a crack and a dent is made on an electrical conductor such as a metal plate or a metal tube, an excitation coil and a receiving coil are disposed in the vicinity of a surface of the conductor and an alternating voltage is applied to the excitation coil. In the conductor, an eddy current occurs. In the receiving coil, an electromotive force is induced. Based on the electromotive force in the receiving coil, which is a detection signal, presence or non-presence of a flaw is determined. The detection signal represents the state of a composite or resultant magnetic field that is the sum of a primary magnetic field and a secondary magnetic field, at a position where the receiving coil is disposed. The primary magnetic field is generated by the excitation coil. The secondary magnetic field is generated by the eddy current. Depending on presence or non-presence of a flaw in a path of the eddy current in the conductor, the eddy current and the secondary magnetic field vary, and thus the detection signal of the receiving coil changes.

In a flaw detection method where an excitation coil and a receiving coil are provided independently of each other, there are two manners of positioning the excitation coil relative to a flaw detected surface of an electrical conductor, namely, a manner to have an excitation coil surface parallel to the flaw detected surface of the conductor, and a manner to have the excitation coil surface perpendicular to the flaw detected surface. The former, parallel disposition manner is disclosed in Patent Document 1, for example. The latter, perpendicular disposition manner is exemplified in Patent Document 2.

When a flaw in a metal tube is to be detected, there is known a method where an excitation coil and a receiving coil that are annular are inserted in the metal tube and disposed concentrically. This method is exemplified in Patent Document 3.

Patent Document 1: JP 2003-149209 A
Patent Document 2: JP 2003-344362 A
Patent Document 3: JP 5-52816 A

DISCLOSURE OF INVENTION

Problem of the Background Art

When flaw detection is made using an eddy current as described above, it is typical to detect a flaw located in the vicinity of a flaw detected surface of the conductor, or a surface in the vicinity of which the excitation coil and the receiving coil are disposed. When a flaw is located remote from the flaw detected surface or in the vicinity of a back surface of the conductor, a change in the detection signal of the receiving coil is small and it is difficult to detect the flaw. It is desired to enable to easily detect even a flaw in the vicinity of the back surface and remote from the flaw detected surface of the conductor.

Study Conducted for Solving the Problem

1. Conception

In the case in which a conductor is disposed in a primary magnetic field generated by an excitation coil, generally the change in the detection signal of a receiving coil due to a flaw is large when the flaw is present in a portion of the conductor where the eddy current density is high. To facilitate detecting a flaw in the vicinity of the back surface of the conductor, it is necessary to increase the eddy current density in the vicinity of the back surface of the conductor.

Taking account of the physical laws describing relationships between magnetism and electrical current and results of experiments, it is recognized that in a conductor located in a magnetic field, the eddy current density becomes high at a place where the magnitude or the direction of the magnetic field, or the magnitude of the magnetic flux density or the direction of a magnetic flux or lines of magnetic force, sharply changes. Thus, the inventor planned to aim at obtaining a desired distribution of the eddy current in a conductor by elaborating the mode of distribution of a primary magnetic field from an excitation coil.

2. Consideration 1 on Distribution Mode of Primary Magnetic Field and Eddy Current (See FIGS. 1 to 6)

2.1 Conventional Parallel Disposition Manner (See FIGS. 1 and 2)

In the manner where a coil surface of an excitation coil 1 is made parallel to a surface of a conductor 2 or a flaw detected surface, primary magnetic fields 3 with different polarities occur around left-hand and right-hand parallel coil segments or two current lines of the excitation coil 1 having a rectangular frame-like shape. Lower portions of the left and right primary magnetic fields 3 intersect with the conductor 2, as shown in FIGS. 1 and 2. In a non-magnetic metal plate 2 as the conductor, an eddy current 4 flows along the current lines of the excitation coil 1, and secondary magnetic fields 5 occur around the path of the eddy current 4.

In FIGS. 1 and 2, the density of the eddy current 4 is represented by contour lines. At a place where the eddy current density is high, the interval between the contour lines is small. In FIG. 2, which shows a cross-section taken along a line A-A in FIG. 1, the eddy current density in the cross-section is indicated by a chain line, and the primary magnetic fields 3 and the secondary magnetic fields 5 in the cross-section are represented using lines of magnetic force. With regard to the secondary magnetic fields 5, only upper portions thereof are shown. At a place where the magnetic flux density is high, the interval between the lines of magnetic force is small.

The lines of magnetic force of the primary magnetic fields 3 are such that in the vicinity of the flaw detected surface of the conductor 2 at a position in the vicinity of each of the current lines of the excitation coil 1, the curvature of the lines of magnetic force is large, or the radius thereof is small, and the rate of change in the direction thereof is high. On the other hand, in the vicinity of the back surface of the conductor 2, the curvature is small and the rate of change in the direction is low. The eddy current density is high in the vicinity of the flaw detected surface of the conductor 2, and low in the vicinity of the back surface. It is difficult to detect a flaw in the vicinity of the back surface of the conductor 2.

2.2 Conventional Perpendicular Disposition Manner (See FIGS. 3 and 4)

In the manner where the coil surface of the excitation coil 1 is arranged perpendicular to the surface of the conductor 2 or the flaw detected surface, primary magnetic fields 3 with different polarities occur around upper and lower parallel coil segments or two current lines of the excitation coil 1 having a rectangular frame-like shape. A lower portion of the lower primary magnetic field 3 intersects with the conductor 2, as shown in FIGS. 3 and 4. In a non-magnetic metal plate 2 as the conductor, an eddy current 4 flows along the lower current line of the excitation coil 1 and a left edge and a right edge of the rectangular conductor 2. A secondary magnetic field 5 occurs around the path of the eddy current 4.

FIGS. 3 and 4 show in the same way as in FIGS. 1 and 2, the density of the eddy current 4, the primary magnetic fields 3, and the secondary magnetic field 5. In FIG. 4, with regard to the eddy current density and the secondary magnetic field 5, only central portions thereof in a left-right direction are shown.

The lines of magnetic force of the primary magnetic fields 3 are such that their curvature is large and their direction change rate is high in the vicinity of the flaw detected surface of the conductor 2 at a position in the vicinity of the current lines of the excitation coil 1. On the other hand, the curvature is small and the direction change rate is low in the vicinity of the back surface of the conductor 2. The eddy current density is high in the vicinity of the flaw detected surface of the conductor 2, and low in the vicinity of the back surface.

2.3 Manner According to Invention (See FIGS. 5 and 6)

The mode of distribution of primary magnetic fields generated by an excitation coil is modified by means of an iron core. The iron core 6 is made of soft magnetic material, which is a ferrite core, and is gate-shaped in cross section, as shown in FIGS. 5 and 6. Around a leg portion at a side, namely, a right one of two leg portions of the iron core 6, an electric wire is wound to form an excitation coil 1. In other words, the excitation coil 1 has a rectangular frame-like shape, and a coil segment thereof at a side, namely, a left-hand coil segment thereof, is disposed on an inner side of the iron core 6, and a right-hand coil segment thereof is disposed on an outer side of the iron core 6. More specifically, the excitation coil 1 is disposed with its coil surface parallel to the surface of the conductor 2 or the flaw detected surface. The coil segment on the inner side of the iron core 6 is on the side of the right leg portion of the iron core 6, and in contact with an inner surface of the right leg portion and separated from an inner surface of the left leg portion. The coil segment on the outer side of the iron core 6 is in contact with an outer surface of the right leg portion of the iron core 6.

That is, on the left, right and upper sides of the coil segment on the inner side of the iron core 6, the iron core 6 that is ferromagnetic is present. More specifically, on the left side of and separated from the coil segment on the inner side of the iron core 6 is located the left leg portion of the iron core 6. On the right side of the coil segment on the inner side of the iron core 6, the right leg portion of the iron core 6 is disposed in contact therewith. On the upper side on the inner side of the iron core 6, a beam portion of the iron core 6 is located. Around the current line of the coil segment on the inner side of the iron core 6, there is formed a magnetic circuit that passes through the right leg portion, the beam portion, and the left leg portion of the iron core 6, and left and lower sides of the iron core 6. A primary magnetic field 3 around the coil segment on the inner side of the iron core 6 is such that lines of magnetic force pass along the magnetic circuit, and the shape thereof is elongated leftward and displaced downward as compared to the case where the iron core is not used. In the vicinity of the flaw detected surface of the conductor 2 at a position in the vicinity of the iron core 6, the lines of magnetic force of the primary magnetic field 3 are small in curvature and low in direction change rate, and an unevenness among the intervals between the lines of magnetic force is small and a rate of change in the magnetic flux density is low. On the other hand, in the vicinity of the back surface of the conductor 2, the curvature is large and the direction change rate is high. The density of the eddy current 4 is high in the vicinity of the back surface of the conductor 2.

On the other hand, on the left side of the coil segment on the outer side of the iron core 6, there are located the right leg portion and the beam portion of the ferromagnetic iron core 6. Around the current line of the coil segment on the outer side of the iron core 6, there is formed a magnetic circuit that passes through the right leg portion and the beam portion of the iron core 6 and upper and right sides of the iron core 6. A primary magnetic field 3 around the coil segment on the outer side of the iron core 6 is such that lines of magnetic force pass along the magnetic circuit, and the shape of the primary magnetic field 3 is displaced upward away from the conductor 2 as compared to the case where the iron core is not used. This primary magnetic field 3 has less power to generate an eddy current in the conductor 2.

That is, in the vicinity of the back surface of the conductor 2 as an object of flaw detection and at a position in the vicinity of the iron core 6, there occurs a place where the eddy current density is high. More specifically, a place where the eddy current density is high is produced, in the vicinity of the back surface of the conductor 2, on the lower side of the iron core 6 gate-shaped in cross section, and at a position where is shifted slightly toward the left side of the iron core 6, which is opposite to the side of the iron core 6 on which the coil segment on the outer side of the iron core 6 is disposed. Therefore, it is supposed that in the rectangular frame-like excitation coil 1, when two opposite coil segments are disposed on the inner side and on the outer side of the iron core 6, respectively, and the receiving coil is located on a side opposite to the coil segment on the outer side of the iron core 6, the ability to detect a flaw in the vicinity of the back surface of the conductor 2 will enhance.

3. Experiment 1 of Flaw Detection Ability (See FIG. 7)

A flaw is detected by scanning a surface of a conductor 2, in each of the manner of the invention and the conventional manners. The conductor 2 is a non-magnetic metal plate with a relative magnetic permeability of approximately 1, and is an aluminum plate. On a back surface of the conductor 2 is present a dent. The thickness of the metal plate is 3.2 mm, and 1 mm at a thin portion where the dent is present. The length of the dent is 67.5 mm. The voltage applied to a coil 1 of an exciting device is a sinusoidal alternating voltage with a frequency of 2 kHz. As an alternating signal detected by a coil 7 of a receiving device, voltage value is measured.

3.1 Manner According to the Invention

According to the manner of the invention, as shown in an upper part of FIG. 7, two opposite coil segments of the excitation coil 1 are disposed on the inner and outer sides of an iron core 6, respectively, and the receiving coil 7 is disposed on a side opposite to the coil segment on the outer side of the iron core 6. In a middle part of FIG. 7, the voltage value is represented by a solid line in correspondence with position in the metal plate 2 as shown in the upper part of the same drawing. The detected voltage value much increases at the thin portion of the metal plate 2, and abruptly changes at a step portion at an edge of the thin portion. As the detected position approaches the dent, the detected voltage value sharply changes. The rate of the detected voltage value at the place where the dent is present to that at a place where the dent is not present is high.

3.2 Conventional Perpendicular Disposition Manner

The conventional perpendicular disposition manner is shown in a lower part of FIG. 7. In the middle part of FIG. 7, the detected voltage value is represented by a broken line in correspondence with position in the metal plate 2 as shown in the lower part of the same drawing. The detected voltage value increases at the thin portion of the metal plate 2, and gently changes at the step portion at the edge of the thin portion. The change in the detected voltage value as approaching the dent is moderate. The rate of change in the detected voltage value due to presence of a dent is lower than that in the manner of the invention.

3.3 Conventional Parallel Disposition Manner

In the conventional parallel disposition manner, too, the detected voltage value increases at the thin portion of the metal plate, and changes at the step portion at the edge of the thin portion. However, the change is further moderate than in the perpendicular disposition manner.

3.4 Conclusion

Compared to the conventional manners, the manner of the invention makes more noticeable the change in the detection signal of the receiving device due to presence of a dent on the back surface of the metal plate, and succeeds in enhancing the flaw detection ability.

4. Consideration 2 on Distribution Mode of Primary Magnetic Field and Eddy Current (See FIGS. 8 to 11)

In the manner of the invention exemplified in FIGS. 5 and 6, when the number of turns of the electric wire of the excitation coil 1 is increased, the coil segment on the inner side of the iron core 6 contacts the inner surface of the left leg portion of the iron core 6 and substantially fills up an inner space of the iron core 6, as shown in FIGS. 8 and 9. In such a state, the effect by the excitation coil 1 intensifies, while the effect by the iron core 6 relatively lowers. An amount which the iron core 6 displaces downward and toward the conductor 2 the primary magnetic field 3 around the coil segment on the inner side of the iron core 6 decreases. The density of the eddy current 4 in the vicinity of the back surface of the conductor 2 decreases.

When the coil segment on the inner side of the iron core 6 substantially fills up the inner space of the iron core 6, the excitation coil 1 is disposed with its coil surface tilted, as shown in FIGS. 10 and 11, in order to compensate for the decrease in the effect by the iron core 6. The coil segment on the outer side of the iron core 6 is located above the coil segment on the inner side of the iron core 6 and beside the beam portion of the iron core 6. By this upward displacement of the coil segment on the outer side of the iron core 6, the primary magnetic field 3 around the coil segment on the inner side of the iron core 6 is displaced downward and toward the conductor 2. The density of the eddy current 4 in the vicinity of the back surface of the conductor 2 increases.

5. Consideration 3 on Receiving Coil Disposition Angle (See FIG. 12)

In the manner of the invention, the attention will be focused on a primary magnetic field and a secondary magnetic field in the vicinity of the receiving coil on a side opposite to the coil segment on the outer side of the iron core. In an example shown in FIG. 12, the primary magnetic field 3 and the secondary magnetic field 5 differ from each other in direction of lines of magnetic force at a corner between the iron core 6 and the conductor 2 on the left side of the iron core 6. The directions of the lines of magnetic force of the two magnetic fields 3, 5 are not parallel in the vicinity of the receiving coil 7.

The receiving coil 7 is slightly inclined leftward and away from the iron core 6 from a vertical position to the surface of the conductor 2 such that its coil surface is parallel to the direction of lines of magnetic force of the primary magnetic field 3 and intersects the direction of the lines of magnetic force of the secondary magnetic field 5. By this, in the receiving coil 7, the primary magnetic field 3 does not induce an electromotive force but the secondary magnetic field 5 solely induces an electromotive force. It is noted that in a case where the receiving coil 7 is a cylindrical coil or a solenoid with a plurality of turns as in the case of FIG. 12, the term "coil surface" here refers to that at its axial central position.

That is, when the receiving coil 7 is disposed in a primary-magnetic-field non-sensitive position where the coil surface is parallel to the direction of the lines of magnetic force of the primary magnetic field generated by the coil segment on the inner side of the iron core 6, the receiving coil 7 detects only the state of the secondary magnetic field 5, which changes depending on presence or non-presence of a flaw. The change in the detection signal of the receiving coil 7 caused by a flaw is made more noticeable. This is supposed to enhance the flaw detection ability.

When the primary-magnetic-field non-sensitive position of the receiving coil 7 is to be found, the conductor 2 is separated away from the excitation coil 1, the iron core 6, and the receiving coil 7, so as to place the receiving coil 7 in a state to detect only the primary magnetic field. In this state, the receiving coil 7 is inclined toward and away from the iron core 6 to determine an angle at which the detected electromotive force becomes zero or minimum. That angle corresponds to the primary-magnetic-field non-sensitive position. By studying a relationship between the disposition angle and the detection signal of the receiving coil 7, it is possible to find its primary-magnetic-field non-sensitive position, which is its optimal disposition angle.

6. Experiment 2 of Receiving Coil Disposition Angle (See FIGS. 13 and 14)

In the manner of the invention exemplified in FIG. 12, the disposition angle θ of the coil 7 of the receiving device, which is an angle formed between an axial direction of the coil 7 and the surface of the conductor 2, is set at various values. For each of the values of the disposition angle θ of the receiving coil 7, a relationship between the thickness of the metal plate 2 of the conductor and the detected voltage value of the receiving device is obtained.

6.1 Aluminum Plate (See FIG. 13)

The metal plate 2 is a non-magnetic aluminum plate having a relative magnetic permeability of approximately 1. The voltage applied to the coil 1 of the exciting device is a sinusoidal alternating voltage of 800 Hz frequency. The electric current flowing through the excitation coil 1 is 172 mA. The optimal disposition angle of the receiving coil 7 is 83 degrees.

The result of the experiment is shown in FIG. 13. When the disposition angle θ of the receiving coil 7 is 80 and 83 degrees, the thickness of the metal plate and the detected voltage value are in one-to-one correspondence, or in a proportional relationship, and a change in the detected voltage value with the thickness of the metal plate is easily noticeable. The flaw detection ability is high. When the disposition angle θ is 70 and 90 degrees, the flaw detection ability is not high.

A relationship between the frequency of the excitation voltage applied to the coil 1 and a detectable range of the thickness of the metal plate or flaw depth will be additionally described. In the result of the experiment shown in FIG. 13, even when the disposition angle θ of the receiving coil 7 is close to 83 degrees that is the optimal value, as the thickness of the metal plate 2 increases to a level close to 3 mm, the rate of change in the detected voltage value to change in the thickness of the metal plate decreases, meaning that this level corresponds to an upper limit of the detectable range. However, when the frequency of the excitation voltage is decreased, the upper limit of the detectable range increases. On the other hand, when the frequency of the excitation voltage is increased, the upper limit of the detectable range decreases, while the rate of change in the detected voltage value to change in the thickness of the metal plate increases and the detection precision becomes high.

6.2 Stainless Steel Plate (See FIG. 14)

The metal plate 2 is a non-magnetic austenitic stainless steel plate having a relative magnetic permeability of approximately 1. The voltage applied to the coil 1 of the exciting device is a sinusoidal alternating voltage of 6 kHz frequency. The electric current flowing through the excitation coil 1 is 70 mA and 103 mA. The optimal disposition angle of the receiving coil 7 is 83 degrees.

The result of the experiment is shown in FIG. 14. When the current of the excitation coil is 70 mA and the disposition angle θ of the receiving coil 7 is 80 and 83 degrees, the thickness of the metal plate and the detected voltage value are in one-to-one correspondence, or in a proportional relationship, and a change in the detected voltage value with the thickness of the metal plate is easily noticeable. The flaw detection ability is high. When the disposition angle θ is 70 degrees, the flaw detection ability is not high.

When the current of the excitation coil is 103 mA and the disposition angle θ of the receiving coil 7 is 80 and 83 degrees, the thickness of the metal plate and the detected voltage value are in one-to-one correspondence, or in a proportional relationship, and a change in the detected voltage value with the thickness of the metal plate is easily noticeable. The flaw detection ability is high.

In the result of the experiment shown in FIG. 14, even when the disposition angle θ of the receiving coil 7 is close to 83 degrees that is the optimal value, as the thickness of the metal plate 2 increases to a level close to 6 mm, the rate of change in the detected voltage value to change in the thickness of the metal plate decreases, meaning that this level corresponds to an upper limit of the detectable range. A decrease in the frequency of the excitation voltage expands the detectable range. On the other hand, an increase in the frequency of the excitation voltage enhances the detection precision. It is noted that in the embodiments of the invention, the frequency of the excitation voltage can be set within a range of 20 Hz to 100 kHz.

6.3 Conclusion

In the manner of the invention, when the receiving coil is disposed in the primary-magnetic-field non-sensitive position or at the disposition angle at which the coil surface is parallel to the direction of the lines of magnetic force of the primary magnetic field generated by the coil segment on the inner side of the iron core, the change in the detection signal of the receiving coil due to a flaw becomes more noticeable. The flaw detection ability is enhanced.

7. Flaw Detection on Tube

When flaw detection is performed on a tube using the manner of the invention, a tube internal fitting method exemplified in FIGS. 24 and 25 or in FIG. 26 is employed. An iron core 64 of an exciting device 61 has an annular shape such that the iron core 64 is concentrically fitted in a tube 50, and is gate-shaped in cross section with a groove formed on an outer circumferential surface thereof. The exciting device 61 has two separate coils 62, 63 each of which is annular and which are fitted concentrically in the tube 50. The two annular excitation coils 62, 63 correspond to the two opposite coil segments of the excitation coil 1 in the rectangular frame-like shape, that is, the left-side and right-side current lines in which a current flows in opposite directions. The excitation coil 62 corresponding to the left-side current line is disposed in the groove of the iron core 64. The excitation coil 63 corresponding to the right-side current line is disposed on the outer side of the iron core 64. A receiving device 71 is disposed on a side opposite to the excitation coil 63 on the outer side of the iron core 64, in the primary-magnetic-field non-sensitive position.

A tube external fitting method is exemplified in FIGS. 27 and 28 or in FIG. 29. An iron core 84 of an exciting device 81 is formed in an annular shape such that the iron core 84 is concentrically fitted on an outer side of a tube 76, and is gate-shaped in cross section with a groove formed on an inner circumferential surface thereof. The exciting device 81 has two separate coils 82, 83 each of which is annular and which are fitted concentrically on the outer side of the tube 76. The two annular excitation coils 82, 83 correspond to the two opposite coil segments of the excitation coil 1 in the rectangular frame-like shape, that is, the left-side and right-side current lines in which a current flows in opposite directions. The excitation coil 82 corresponding to the left-side current line is disposed in the groove of the iron core 84. The excitation coil 83 corresponding to the right-side current line is disposed on the outer side of the iron core 84. A receiving device 91 is disposed on a side opposite to the excitation coil 83 on the outer side of the iron core 84, in the primary-magnetic-field non-sensitive position.

When the exciting device is fitted on a solid bar instead of a hollow tube, the same tube external fitting method is employed.

Means for Solving the Problem (1) An eddy-current flaw detection method in which an exciting device and a receiving device are disposed in the vicinity of a conductor, which is a subject of the flaw detection, and an eddy current is generated in the conductor by a primary magnetic field generated by the exciting device to generate a secondary magnetic field, the state of the magnetic field is detected by the receiving device to detect the flaw based on a detection signal of the receiving device, the method being characterized in that:

the exciting device includes an excitation coil and an iron core, the excitation coil having a first current line and a second current line in which an electric current flows in opposite directions, the iron core being gate-shaped in cross section and having a first leg portion, a second leg portion, and a beam portion connecting the two leg portions, an opening of the iron core on a side opposite to the beam portion facing toward the conductor, the first current line being disposed on an inner side of the first leg portion and the second leg portion of the iron core, and the second current line being disposed on an outer side of the first leg portion of the iron core, a magnetic circuit is formed around the first current line on the inner side of the iron core and passes through the first leg portion, the beam portion, and the second leg portion of the iron core, and the conductor, and a magnetic circuit is formed around the second current line on the outer side of the iron core and passes through the first leg portion and the beam portion of the iron core, and the receiving device is disposed in a corner between the second leg portion of the iron core and the conductor, on a side opposite to the second current line on the outer side of the iron core.

(2) The eddy-current flaw detection method as described in (1), characterized in that:

the receiving device is disposed at a position substantially not to detect the state of a primary magnetic field generated by the first current line on the inner side of the iron core, and detects the state of the secondary magnetic field.

(3) An eddy-current flaw detection apparatus in which an exciting device and a receiving device are disposed in the vicinity of a conductor, which is a subject of the flaw detection, and an eddy current is generated in the conductor by a primary magnetic field generated by the exciting device to generate a secondary magnetic field, the state of the magnetic field is detected by the receiving device to detect the flaw based on a detection signal of the receiving device, the apparatus being characterized in that:

the exciting device and the receiving device are disposed in a casing that is a non-magnetic insulator, the casing includes a sensing surface, which is contacted with or held in the vicinity of a flaw detected surface of the conductor, the exciting device includes an excitation coil and an iron core, the excitation coil having a first current line and a second current line in which an electric current flows in opposite directions, the iron core being gate-shaped in cross section and having a first leg portion, a second leg portion, and a beam portion connecting the two leg portions, an opening of the iron core on a side opposite to the beam portion facing toward the sensing surface, ends of the two leg portions being disposed in the vicinity of the sensing surface, the first current line being disposed on an inner side of the first leg portion and the second leg portion of the iron core, and the second current line being disposed on an outer side of the first leg portion of the iron core, and the receiving device is disposed in a corner between the second leg portion of the iron core and the sensing surface, on a side opposite to the second current line on the outer side of the iron core, with an end of the receiving device being disposed in the vicinity of the sensing surface.

(4) The eddy-current flaw detection apparatus as described in (3), characterized in that:

the first current line on the inner side of the iron core substantially fills up an inner space of the iron core, and the second current line on the outer side of the iron core is disposed beside the beam portion of the iron core.

(5) The eddy-current flaw detection apparatus as described in (3) or (4), characterized in that:

the receiving device is disposed at a position substantially not to detect the state of a primary magnetic field generated by the first current line on the inner side of the iron core.

(6) The eddy-current flaw detection apparatus as described in any one of (3) through (5), characterized in that:

the iron core of the exciting device has an elongate shape long in a direction of a normal to the gate-shaped cross section, and the excitation coil of the exciting device has an elongate frame-like shape and is fitted on the first leg portion of the iron core, and a plurality of the receiving devices are arranged along a longitudinal direction of the exciting device and spaced from one another.

(7) The eddy-current flaw detection apparatus as described in any one of (3) through (5), characterized in that:

a plurality of the iron cores of the exciting device are arranged along a direction of a normal to the gate-shaped cross section of the iron cores and spaced from one another, the excitation coil of the exciting device has an elongate frame-like shape and is fitted on the first leg portions of the plurality of the iron cores, and the receiving device is disposed on an outer side of the second leg portion of each of the iron cores of the exciting device, each of the iron cores of the exciting device is paired with the receiving device disposed on the outer side of the second leg portion of the iron core, and the pairs of the iron cores and the receiving devices are arranged along the direction of the normal to the gate-shaped cross section of the iron cores, and the casing and the excitation coil are bendable between each two adjacent pairs of the iron cores and the receiving devices, and the casing in which the exciting device and the receiving devices are disposed is bendable such that a shape thereof in the direction of the normal to the gate-shaped cross section of the iron cores conforms to a curve of the flaw detected surface of the conductor.

(8) The eddy-current flaw detection apparatus as described in any one of (3) through (5), characterized in that:

the casing is shaped to be fitted in a tube as the conductor, and the sensing surface of the casing is provided by an outer circumferential surface of the casing, which faces an inner circumferential surface of the tube, the iron core of the exciting device has an annular shape with a groove formed on an outer circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

(9) The eddy-current flaw detection apparatus as described in any one of (3) through (5), characterized in that:

the casing is shaped to be fitted on an outer side of a tube or a bar as the conductor, and the sensing surface of the casing is provided by an inner circumferential surface of the casing, which faces an outer circumferential surface of the tube or the bar, the iron core of the exciting device has an annular shape with a groove formed on an inner circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

Advantageous Effects

It is enabled to easily detect a flaw even when the flaw is in the vicinity of the back surface of the conductor. The flaw detection ability is enhanced.

Figure 1:
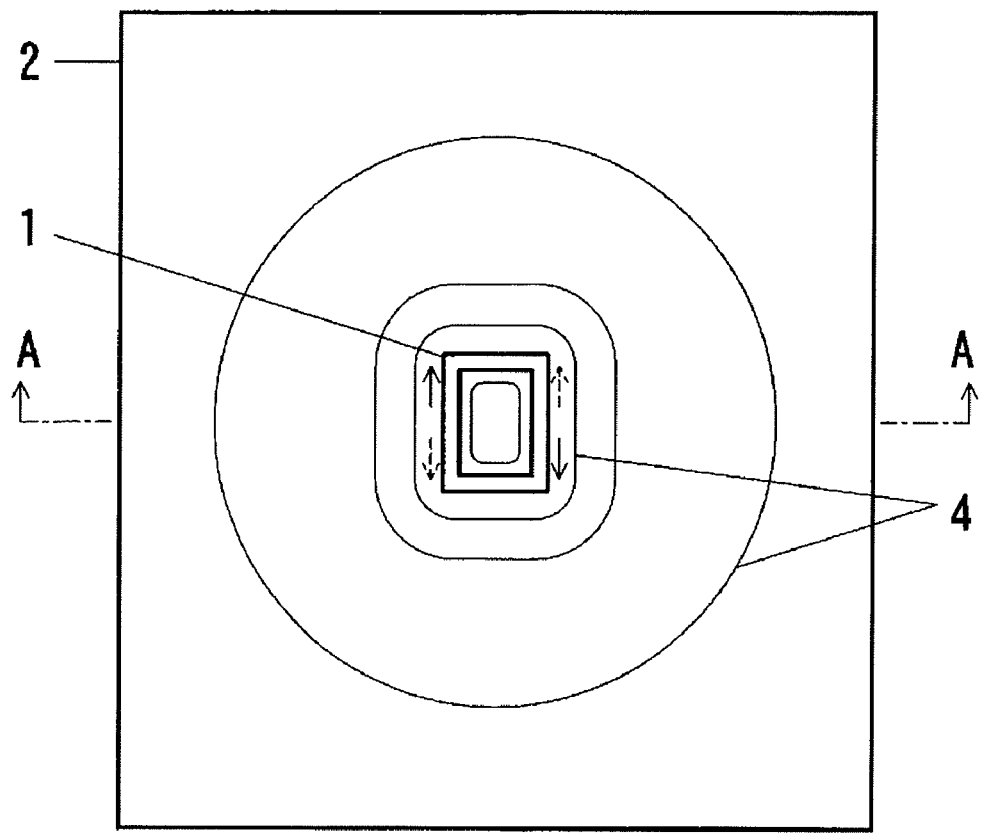
FIG. 1 A schematic plan view illustrating a conventional excitation-coil parallel disposition manner.
Figure 2:
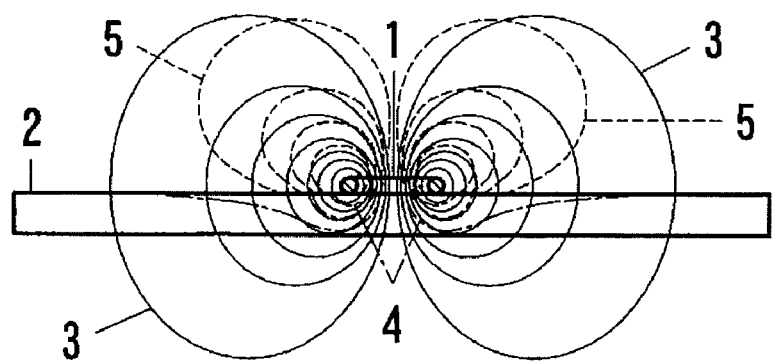
FIG. 2 A schematic front view of the manner, and shows primary magnetic fields, secondary magnetic fields, and an eddy current density as seen in a cross-section taken along a line A-A in FIG. 1.
Figure 3:
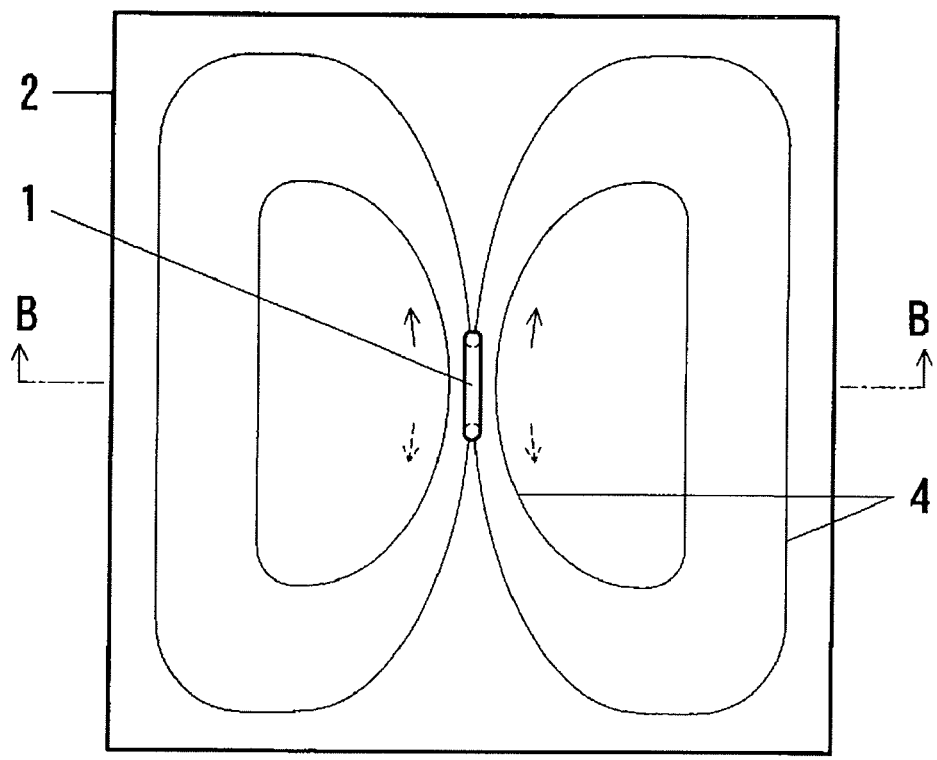
FIG. 3 A schematic plan view illustrating a conventional excitation-coil perpendicular disposition manner.
Figure 4:
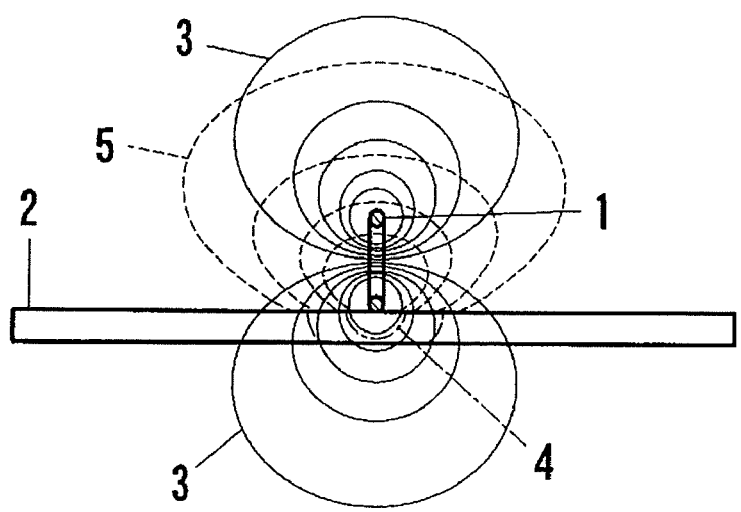
FIG. 4 A schematic front view of the manner, and shows primary magnetic fields, a secondary magnetic field, and an eddy current density as seen in a cross-section taken along a line B-B in FIG. 3.
Figure 5:
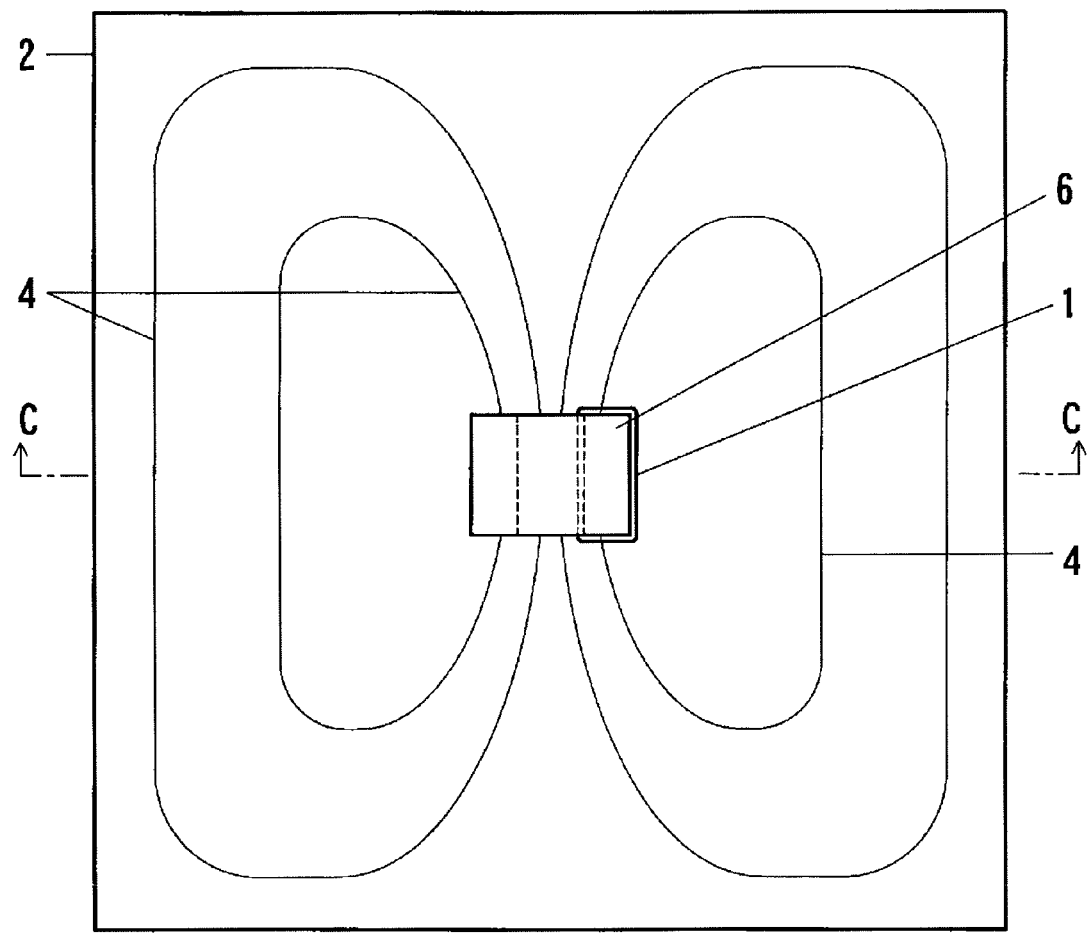
FIG. 5 A schematic plan view exemplifying a manner according to the invention.
Figure 6:
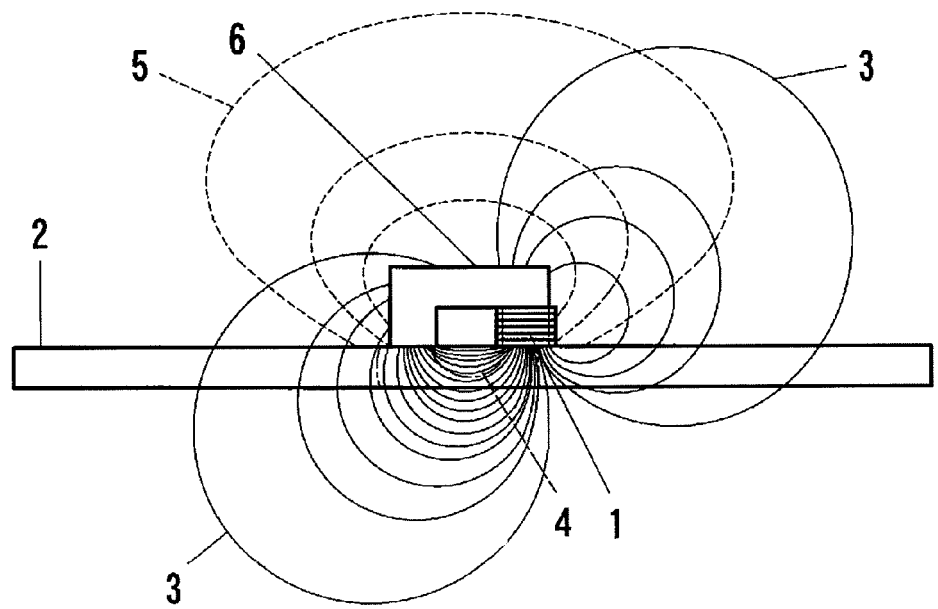
FIG. 6 A schematic front view of the manner, and shows primary magnetic fields, a secondary magnetic field, and an eddy current density as seen in a cross-section taken along a line C-C in FIG. 5.
Figure 7:
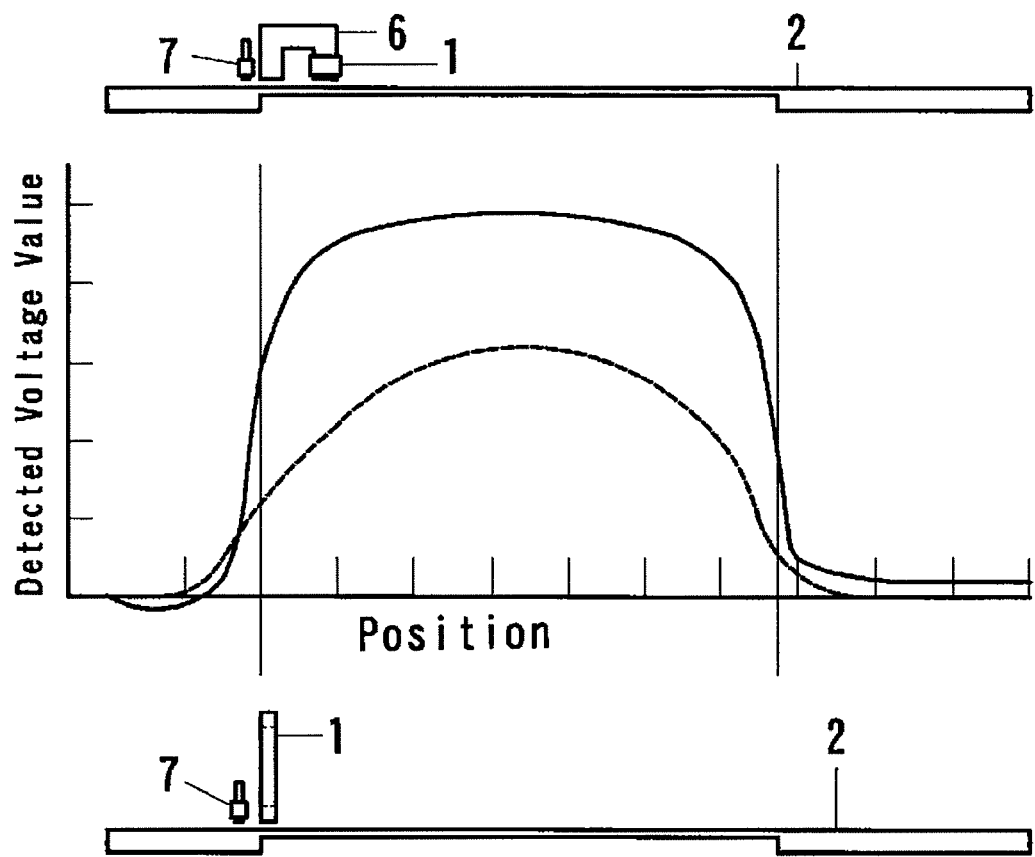
FIG. 7 A view representing a relationship between position in a metal plate with a dent and the detected voltage value of a receiving coil, in the manner of the invention and in a conventional manner.
Figure 8:
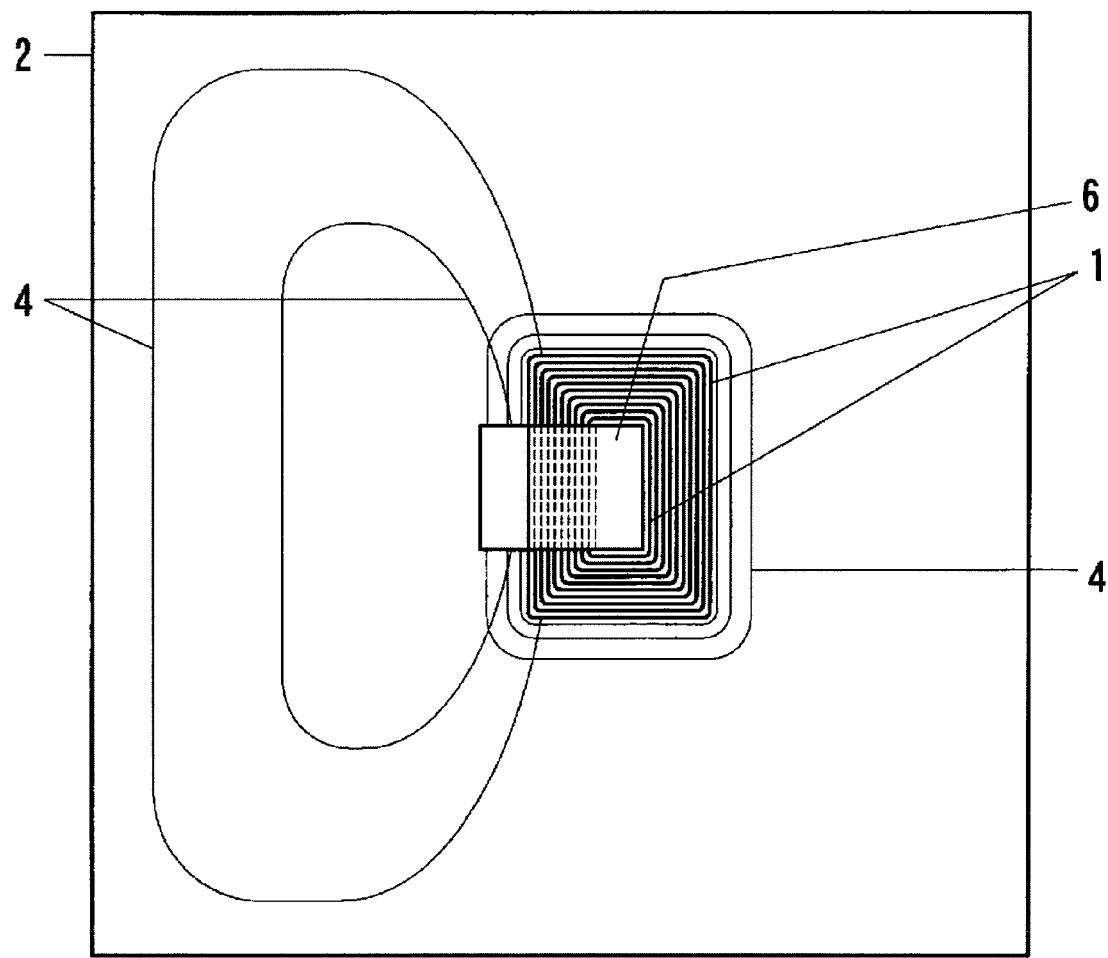
FIG. 8 A schematic plan view exemplifying another manner according to the invention.
Figure 9:
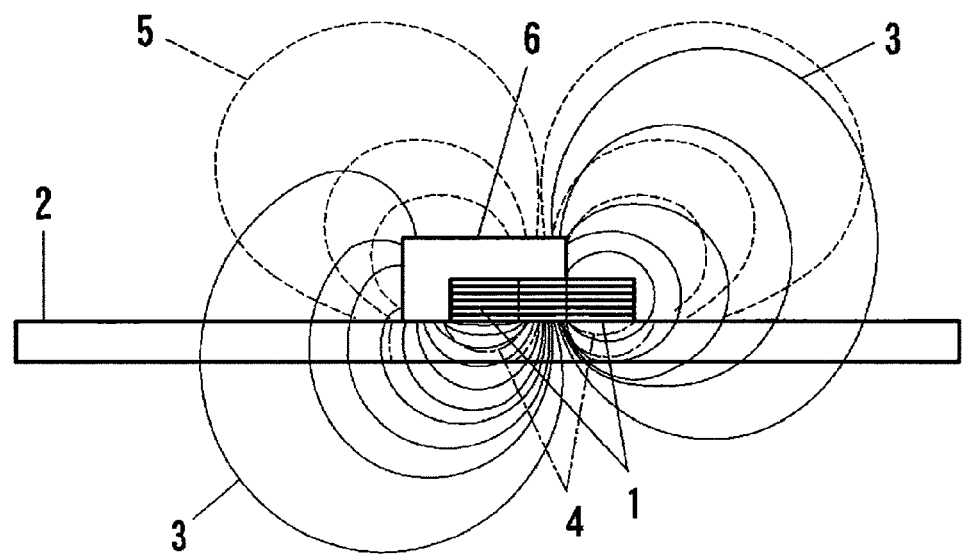
FIG. 9 A schematic front view of the manner, and shows primary magnetic fields, a secondary magnetic field, and an eddy current density as seen in a cross-section taken along a line at a center of FIG. 8.
Figure 10:
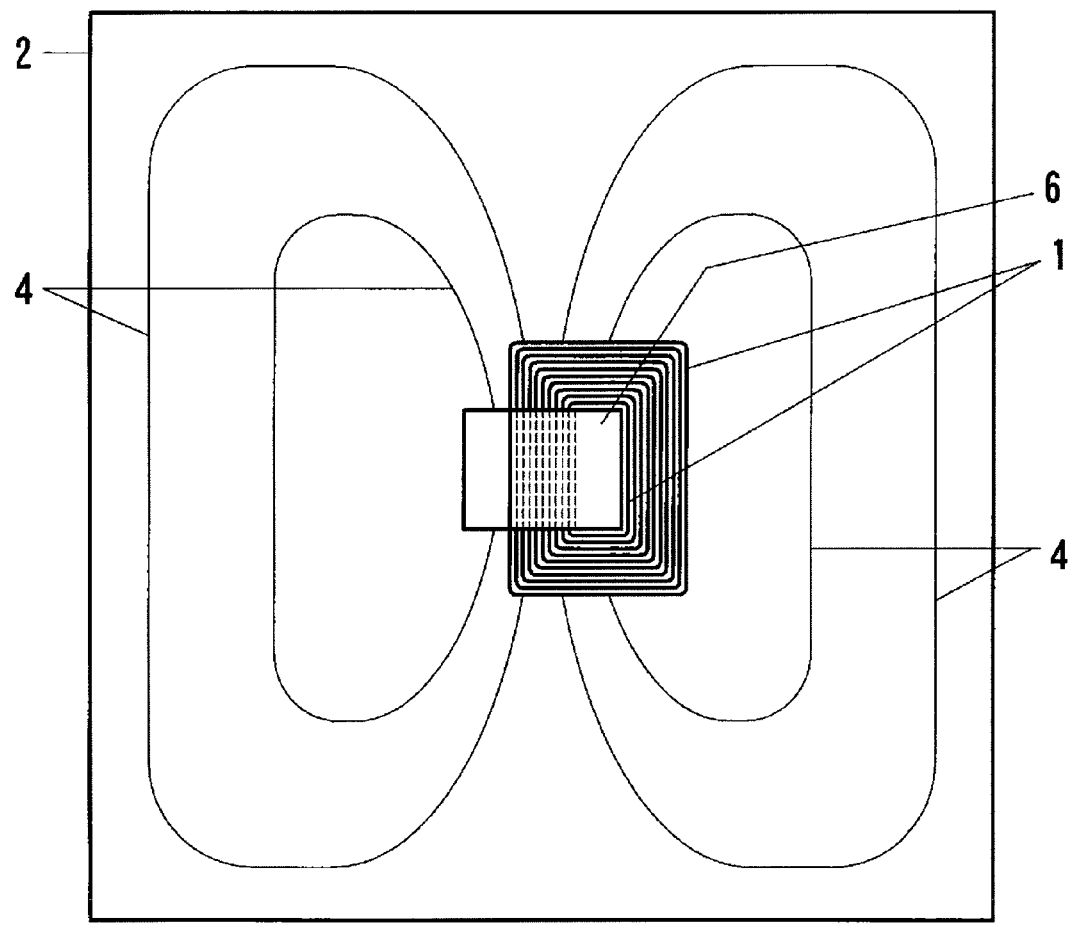
FIG. 10 A schematic plan view exemplifying further another manner according to the invention.
Figure 11:
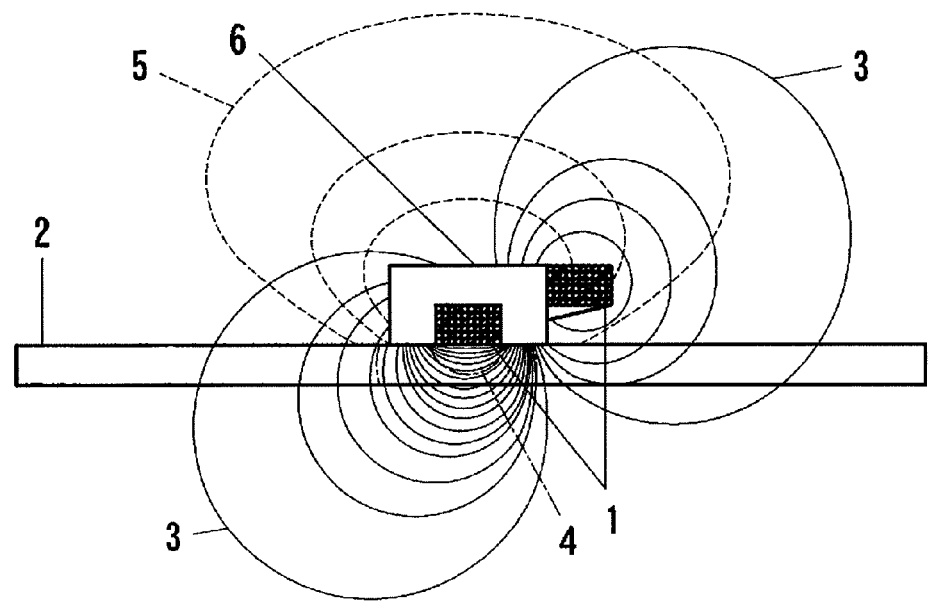
FIG. 11 A schematic front view of the manner, and shows primary magnetic fields, a secondary magnetic field, and an eddy current density as seen in a cross-section taken along a line at a center of FIG. 10.
Figure 12:
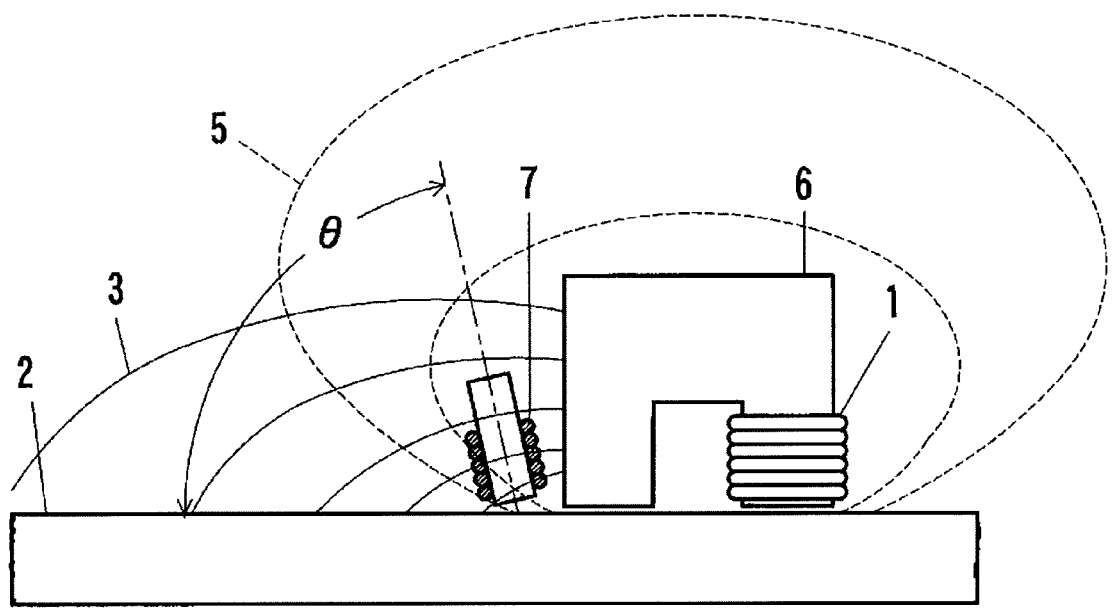
FIG. 12 A schematic front view exemplifying magnetic fields around a receiving coil in the manner of the invention.
Figure 13:
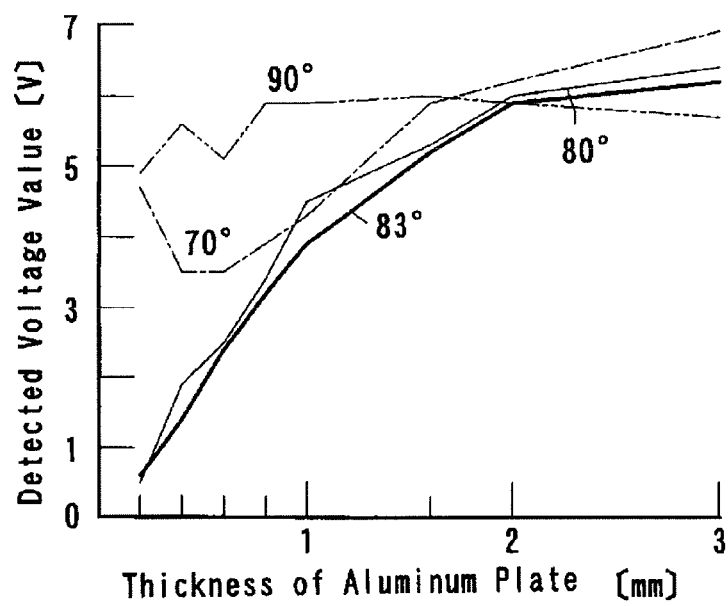
FIG. 13 A graph representing a relationship between the thickness of an aluminum plate and the detected voltage value of a receiving coil for each of various disposition angles of the receiving coil in the manner of the invention.
Figure 14:
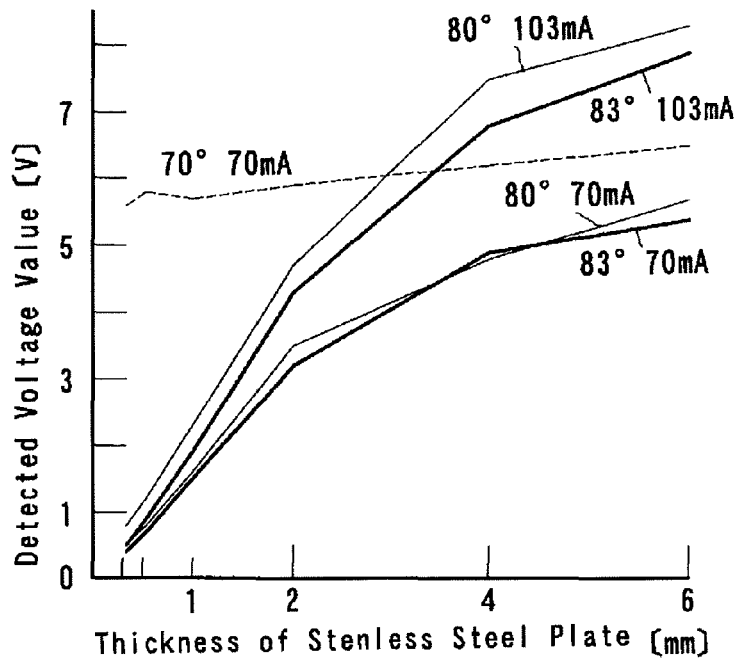
FIG. 14 A graph representing a relationship between the thickness of a stainless steel plate and the detected voltage value of a receiving coil for each of various disposition angles of the receiving coil in the manner of the invention.

EXPLANATION OF REFERENCE 1 excitation coil, coil of exciting device
2 conductor, subject of flaw detection, non-magnetic metal plate
3 primary magnetic field generated by excitation coil
4 eddy current
5 secondary magnetic field generated by eddy current
6 iron core gate-shaped in cross section, ferromagnetic iron core
7 coil of receiving device, receiving coil, solenoid
θ receiving coil disposition angle First and Second Embodiments of the Invention 10 flat plate as non-magnetic metal plate
11 casing
12 lower surface, sensing surface
13 cable
21 exciting device
22 coil, excitation coil
23 first coil segment, first current line
24 second coil segment, second current line
25 iron core gate-shaped in cross section
26 first leg portion
27 second leg portion
28 beam portion
31 receiving device
32 coil, receiving coil
33 iron core Third Embodiment of the Invention 40 curved surface plate as non-magnetic metal plate
41 exciting device
42 iron core gate-shaped in cross section
43 first leg portion
44 second leg portion
45 beam portion
46 slit
47 thin portion Fourth and Fifth Embodiments of the Invention 50 cylindrical tube as non-magnetic metal tube
51 casing
52 outer circumferential surface, sensing surface
53 cable
61 exciting device
62 coil, first excitation coil, first current line
63 coil, second excitation coil, second current line
64 iron core gate-shaped in cross section
65 first leg portion
66 second leg portion
67 beam portion
71 receiving device
72 coil, receiving coil
73 iron core Sixth and Seventh Embodiments of the Invention 76 cylindrical tube as non-magnetic metal tube
77 casing
78 inner circumferential surface, sensing surface
79 cable
81 exciting device
82 coil, first excitation coil, first current line
83 coil, second excitation coil, second current line
84 iron core gate-shaped in cross section
85 first leg portion
86 second leg portion
87 beam portion
91 receiving device
92 coil, receiving coil
93 iron core

BEST MODE FOR CARRYING OUT THE INVENTION

Figure 15:
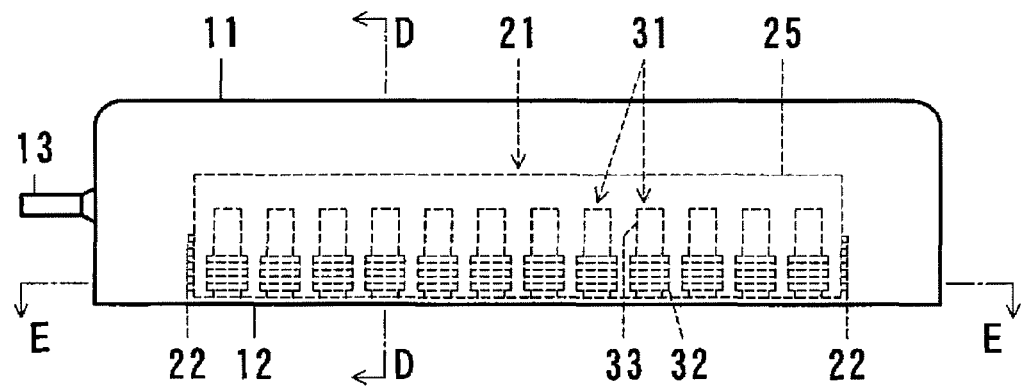
FIG. 15 A front view of an eddy-current flaw detection apparatus for plane surface according to a first embodiment of the invention.
Figure 16:
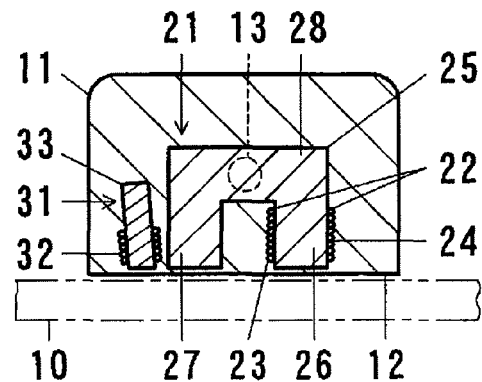
FIG. 16 A cross-sectional view taken along a line D-D in FIG. 15.
Figure 17:
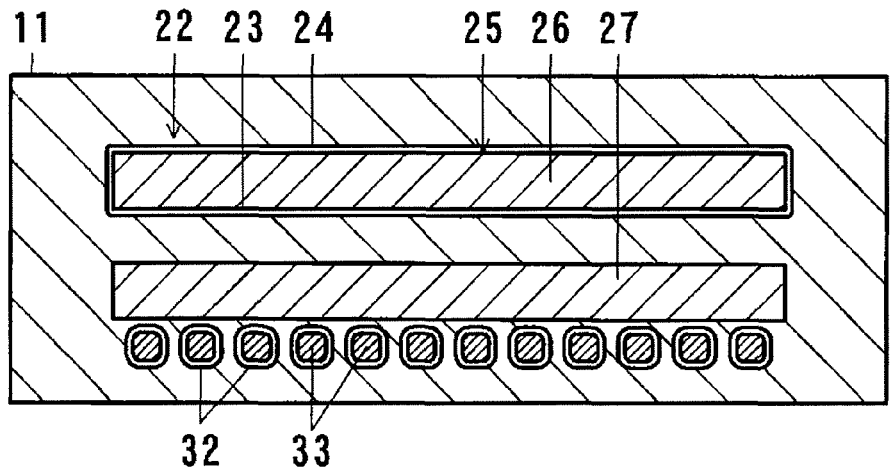
FIG. 17 A cross-sectional view taken along a line E-E in FIG. 15.

First Embodiment (See FIGS. 15 to 17)

The present embodiment is for detecting a flaw in a flat plate 10 as a non-magnetic metal plate.

As shown in FIGS. 15 and 16, an eddy-current flaw detection apparatus for plane surface according to this embodiment has a casing 11 in which an exciting device 21 and a receiving device 31 are disposed. The casing 11 is a non-magnetic insulator formed of synthetic resin. The casing 11 has the shape of a rectangular parallelepiped laterally long, and its lower surface 12 which is a plane surface functions as a sensing surface 12 to be contacted with or brought in the vicinity of a plane surface of the flat plate 10 as a flaw detected surface. At an end of the casing 11 is connected a cable 13 through which conducting wires of the exciting device 21 and the receiving device 31 extend to the external. The exciting device 21 and the receiving device 31 are connected to an exciting circuit and a receiving circuit (neither shown), respectively, via the cable 13.

As shown in FIGS. 16 and 17, the exciting device 21 includes a coil 22 and an iron core 25. The coil 22 is an excitation coil with a plurality of turns and formed in an elongate frame-like shape, and has a first coil segment 23 and a second coil segment 24 that are disposed parallel to each other on opposite sides. The first coil segment 23 and the second coil segment 24 correspond to a first current line 23 and a second current line 24 in which a current flows in opposite directions. The iron core 25 is a ferrite core, an iron core of a soft magnetic material. The iron core 25 has a gate-like cross-sectional shape with a first leg portion 26, a second leg portion 27, and a beam portion 28 connecting upper ends of the two leg portions 26, 27, and is elongated in a direction of a normal to the gate-like cross section.

The laterally long iron core 25 is buried in the casing 11 to extend along a longitudinal direction of the casing 11, and is disposed such that its opening on a side opposite to the beam portion 28 faces to the sensing surface 12 and ends of the two leg portions 26, 27 are located in the vicinity of the sensing surface 12. The laterally long excitation coil 22 is buried in the casing 11 to extend along the longitudinal direction, and fitted on the first leg portion 26 of the iron core 25. On an inner side of the first leg portion 26 and the second leg portion 27, and on an outer side of the first leg portion 26, there are respectively disposed the first current line 23 and the second current line 24. A coil surface including the first current line 23 and the second current line 24 is substantially parallel to the sensing surface 12. The first leg portion 26 and the second leg portion 27 are perpendicular to the sensing surface 12. The excitation coil 22 is thin with a single layer of electric wire turns, and the first coil segment 23 on the inner side of the iron core 25 is on the side of the first leg portion 26 of the iron core 25 and in contact with an inner surface of the first leg portion 26 and off an inner surface of the second leg portion 27. The second coil segment 24 on the outer side of the iron core 25 is in contact with an outer surface of the first leg portion 26.

Around the first current line 23 on the inner side of the iron core 25 is formed a magnetic circuit that passes through the first leg portion 26, the beam portion 28, the second leg portion 27, and the flat plate 10. Around the second current line 24 on the outer side of the iron core 25 is formed a magnetic circuit that passes through the first leg portion 26 and the beam portion 28.

As shown in FIGS. 16 and 17, the receiving device 31 includes a coil 32 and an iron core 33. The coil 32 is a receiving coil with a plurality of turns and has a cylindrical shape. The iron core 33 is a ferrite core, an iron core of a soft magnetic material. The iron core 33 is formed in a bar-like shape, and is concentrically fitted in the receiving coil 32.

The receiving coil 32 with the iron core 33 is buried in the casing 11 at a position on the outer side of the iron core 25 and opposite to the second current line 24, and is disposed almost upright in a corner between the second leg portion 27 of the iron core 25 and the sensing surface 12 with an end thereof located in the vicinity of the sensing surface 12. As shown in FIG. 16, the receiving coil 32 with the iron core 33 is disposed with its axis slightly tilted relative to a vertical direction parallel to the second leg portion 27 of the iron core 25 to a side away from the second leg portion 27 such that a coil surface at an axial central position is parallel to a direction of a magnetic flux of a primary magnetic field. That is, the receiving coil 32 is placed in a primary-magnetic-field non-sensitive position. The receiving device 31 is not in contact with the exciting device 21 and is separated therefrom.

As shown in FIGS. 15 and 17, a plurality of the receiving devices 31 are arranged at constant intervals along the longitudinal direction of the exciting device 21, that is, along a direction of a normal to the gate-shaped cross section of the iron core 25. This makes large the number of places where flaw detection is made.

When flaw detection is performed on the flat plate 10 using the eddy-current flaw detection apparatus of the present embodiment, the sensing surface 12 of the casing 11 is brought into contact with or in the vicinity of the flaw detected surface of the flat plate 10 and held parallel thereto. To the exciting device 21, an alternating voltage is applied. Then, an eddy current flows in the flat plate 10. Each of the receiving devices 31 substantially does not detect the state of the primary magnetic field generated by the excitation coil 22, but detects the state of a secondary magnetic field generated by the eddy current. The casing 11 in which the exciting device 21 and the receiving devices 31 are disposed are moved along the flaw detected surface of the flat plate 10 and in a direction perpendicular to the direction of arrangement of the receiving devices 31, that is, a direction perpendicular to the longitudinal direction of the exciting device 21. When a flaw is present in the flat plate 10, the detected voltage value of a receiving device 31 that is located in the vicinity of the flaw noticeably changes.

Figure 18:
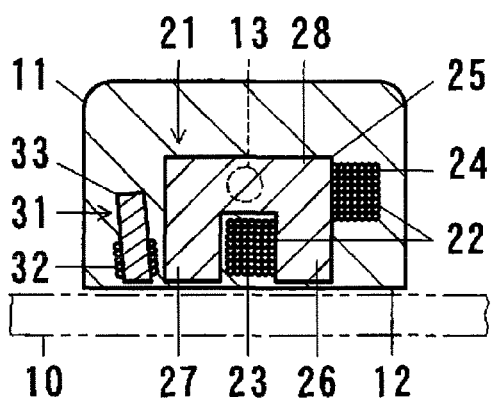
FIG. 18 A cross-sectional view corresponding to FIG. 16, and is a side view of an eddy-current flaw detection apparatus for plane surface according to a second embodiment of the invention.
Figure 19:
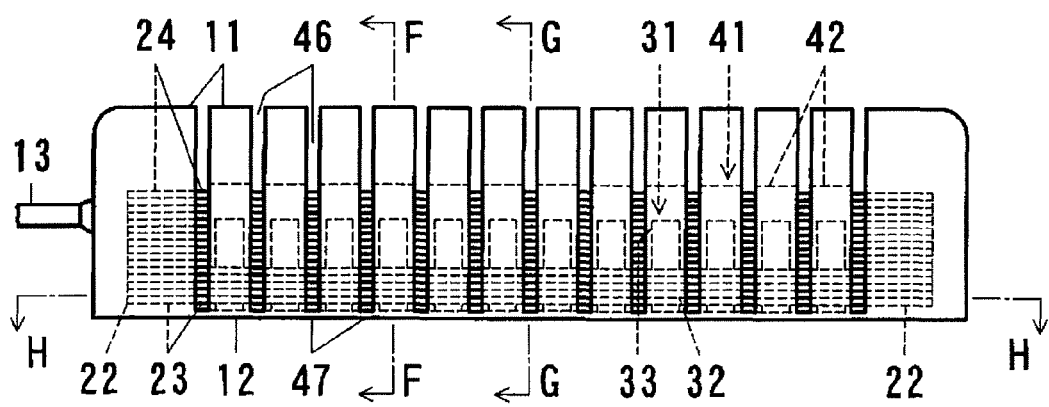
FIG. 19 A front view of an eddy-current flaw detection apparatus for curved surface according to a third embodiment of the invention.
Figure 20:
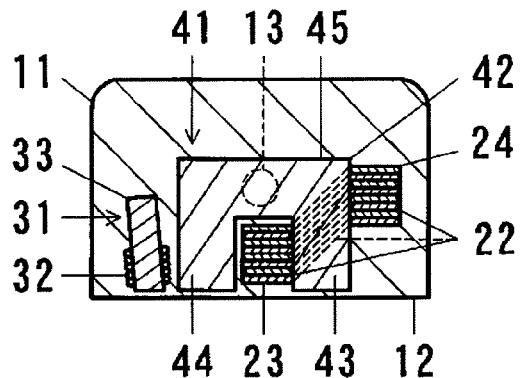
FIG. 20 A cross-sectional view taken along a line F-F in FIG. 19.
Figure 21:
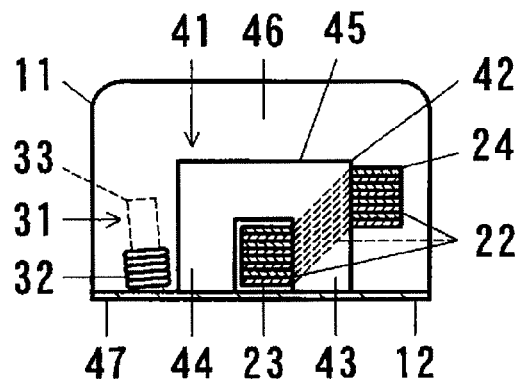
FIG. 21 A cross-sectional view taken along a line G-G in FIG. 19.
Figure 22:
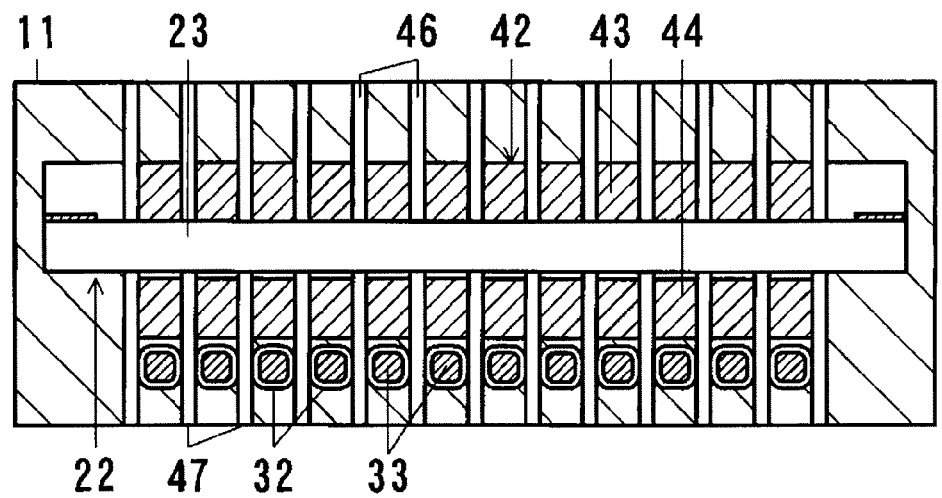
FIG. 22 A cross-sectional view taken along a line H-H in FIG. 19.

Second Embodiment (See FIG. 18)

A second embodiment is slightly modified from the first embodiment. In an eddy-current flaw detection apparatus for plane surface according to the present embodiment, the number of electric wire turns of the excitation coil 22 is increased, and the coil surface of the excitation coil 22 is tilted.

As shown in FIG. 18, the excitation coil 22 is thick with a plurality of layers of electric wire turns. The first coil segment 23 on the inner side of the iron core 25 substantially fills up the space on the inner side of the first leg portion 26 and the second leg portion 27 of the iron core 25. The second coil segment 24 on the outer side of the iron core 25 is located above the first coil segment 23 on the inner side of the iron core 25, and beside the beam portion 28 of the iron core 25. The excitation coil 22 is disposed with its coil surface tilted relative to the sensing surface 12.

In the other parts, the second embodiment is identical with the first embodiment. In the drawing, the same reference numerals are used as in the first embodiment.

Third Embodiment (See FIGS. 19 to 23)

A third embodiment is for detecting a flaw in a curved surface plate 40 as a non-magnetic metal plate.

An eddy-current flaw detection apparatus for curved surface according to the present embodiment is obtained by altering that for plane surface according to the first and second embodiments. There will be chiefly described where change is made.

As shown in FIGS. 19 to 22, an exciting device 41 includes a coil 22 and a plurality of iron cores 42. Unlike the excitation coil 22 of the first and second embodiments which is formed of a linear electric wire or a copper wire with insulating coating, the excitation coil 22 of this embodiment is formed of an electric strip or a phosphor bronze strip with insulating coating. A first coil segment 23 and a second coil segment 24 are formed by vertically stacking the electric strips. Each of the iron cores 42 is gate-shaped in cross section, similar to the iron core 25 in the first and second embodiments, but a dimension in the direction of the normal to the gate-shaped cross section is short. The plurality of iron cores 42 are arranged at constant intervals along a direction of a normal to the gate-shaped cross section, and a single excitation coil 22 in an elongate frame-like shape is fitted on a plurality of first leg portions 43 arranged in a row. The first coil segment 23 on the inner side of the iron cores 42 substantially fills up a space on the inner side of the first leg portions 43 and second leg portions 44 of the iron cores 42. The second coil segment 24 on the outer side of the iron cores 42 is located above the first coil segment 23 on the inner side of the iron cores 42, and beside beam portions 45 of the iron cores 42. The excitation coil 22 is disposed with its coil surface tilted relative to the sensing surface 12.

The receiving device 31 is similar to that in the first and second embodiments, and a plurality of the receiving devices 31 are arranged at constant intervals along the direction of the normal to the gate-shaped cross section of the iron cores 42. The number of the receiving devices 31 and the intervals between the receiving devices 31 are made identical with those of the iron cores 42. In other words, the receiving devices 31 are provided for the respective iron cores 42 of the exciting device 41 and disposed on the outer side of the second leg portions 44 of the corresponding iron cores 42. Each iron core 42 and a receiving device 31 on the outer side of the second leg portion 44 of the iron core 42 are paired, and the pairs each consisting of one of the iron cores 42 and one of the receiving devices 31 are arranged at constant intervals along the direction of the normal to the gate-shaped cross section of the iron cores 42.

The casing 11 has slits 46 formed to extend from its upper surface toward the sensing surface 12 or its lower surface. The slits 46 go through the casing 11 in a front-rear direction. Each slit 46 is thin and is a slot. A plurality of slits 46 are formed, and disposed on the left and right sides of the pairs each consisting of a receiving device 31 and an iron core 42. In other words, the slits 46 are disposed between each two adjacent pairs each consisting of an iron core 42 and a receiving device 31, and on the outer side of each of two pairs at opposite ends of the row of the pairs. The excitation coil 22 is such that its first current line 23 and second current line 24 extend across the slits 46. Portions of the casing 11 between bottom surfaces of the respective slits 46 and the sensing surface 12 constitute thin portions 47, at each of which the casing 11 is bendable. The excitation coil 22 is bendable at each of positions where the first current line 23 and the second current line 24 extend across the slits 46. The casing 11 in which the exciting device 41 and the receiving devices 31 are disposed is bendable such that its shape in the longitudinal direction or in the direction of the normal to the gate-shaped cross section of the iron cores 42 conforms to a curve of a flaw detected surface of the curved surface plate 40.

Figure 23:
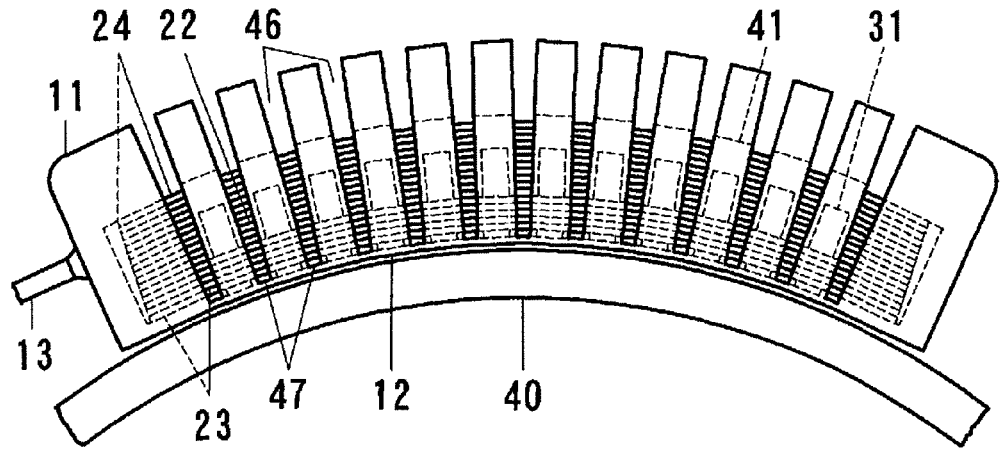
FIG. 23 A front view of the eddy-current flaw detection apparatus in the used state.

When flaw detection is made on the curved surface plate 40 using the eddy-current flaw detection apparatus of this embodiment, the casing 11 in which the exciting device 41 and the receiving devices 31 are disposed is bent with respect to the direction of the normal to the gate-shaped cross section of the iron cores 42, with the sensing surface 12 being on the inner side of the bend, such that the curved surface of the sensing surface 12 conforms to a convex curve of the flaw detected surface of the curved surface plate 40, and the sensing surface 12 is brought into contact with or in the vicinity of the flaw detected surface that is the convex curved surface of the curved surface plate 40 and is made substantially parallel thereto, as shown in FIG. 23. Thereafter, the apparatus is used in the same way as in the first and second embodiments. Since the first coil segment 23 and the second coil segment 24 of the excitation coil 22 are formed by stacking electric strips, it is easy to bend the excitation coil 22 to conform to the convex curve of the curved surface plate 40, or to restore to the flat state. It is noted that when the flaw detected surface of the curved surface plate 40 is a curved surface of shallow concavity, the casing 11 in which the exciting device 41 and the receiving devices 31 are disposed is bent with respect to the direction of the normal to the gate-shaped cross section of the iron cores 42 with the sensing surface 12 being on the outer side of the bend.

In the other parts, the third embodiment is identical with the first and second embodiments. In the drawings, the same reference numerals are used as in the first and second embodiments.

Figure 24:
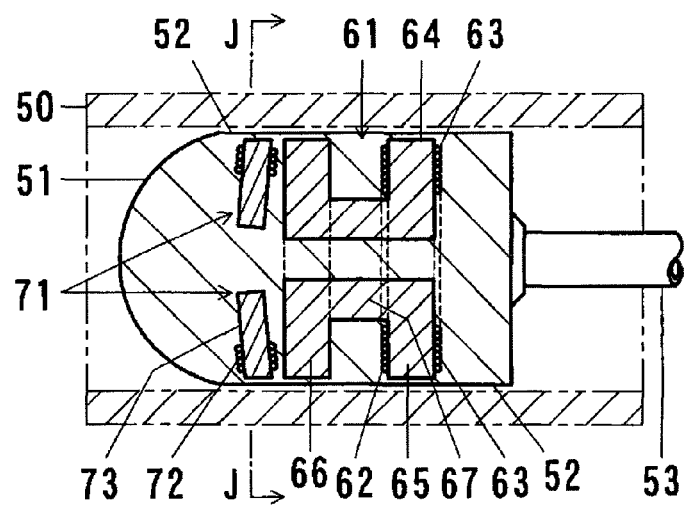
FIG. 24 A sectional side view of an eddy-current flaw detection apparatus of a tube internal fitting method according to a fourth embodiment.
Figure 25:
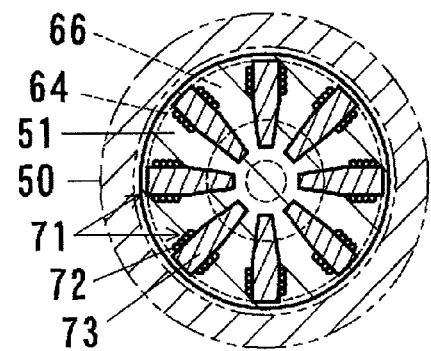
FIG. 25 A cross-sectional view taken along a line J-J in FIG. 24.

Fourth Embodiment (See FIGS. 24 and 25)

A fourth embodiment is for detecting a flaw in a circular tube 50 as a non-magnetic metal tube, and uses a tube internal fitting method.

An eddy-current flaw detection apparatus for circular tube according to the fourth embodiment has a casing 51 in which an exciting device 61 and a receiving device 71 are disposed, as shown in FIGS. 24 and 25. The casing 51 is a non-magnetic insulator formed of synthetic resin. The casing 51 has the shape of a round bar and is concentrically fitted in the circular tube 50, and its outer circumferential surface 52, which is a cylindrical surface, functions as a sensing surface to be contacted with, or located in the vicinity of a cylindrical inner surface of the circular tube 50 as a flaw detected surface. At its front end, the casing 51 protrudes in a semispherical shape. At a rear end of the casing 51 is connected a cable 53 through which conducting wires of the exciting device 61 and the receiving device 71 extend to the external. The cable 53 serves as a push rod for advancing the casing 51 inside the circular tube 50 as well as a pull cord for retracting the casing 51. The exciting device 61 and the receiving device 71 are connected to an exciting circuit and a receiving circuit (neither shown), respectively, via the cable 53.

The exciting device 61 includes coils 62, 63 and an iron core 64. The iron core 64 is a ferrite core, an iron core of soft magnetic material. The iron core 64 is annular, and has a groove concentrically formed on an outer circumferential of the iron core 64, and is gate-shaped in cross section. The iron core 64 has a first leg portion 65 and a second leg portion 66 that are on opposite sides of the groove, and a beam portion 67 connecting ends of the two leg portions 65, 66 on a radially inner side. The coils 62, 63 are excitation coils with a plurality of turns, and are two separate coils, namely, a first excitation coil 62 and a second excitation coil 63. The two excitation coils 62, 63 are annular and have identical dimensions.

The annular iron core 64 is concentrically buried in the casing 51, and disposed such that an opening of the groove on a side opposite to the beam portion 67, that is, on a radially outer side, faces toward the sensing surface 52 and ends of the two leg portions 65, 66 are in the vicinity of the sensing surface 52. The two leg portions 65, 66 are perpendicular to the sensing surface 52. The two annular excitation coils 62, 63 are concentrically buried in the casing 51 and arranged in a front-rear direction. The first excitation coil 62 is disposed in the groove on the inner side of the two leg portions 65, 66 of the iron core 64, and constitutes a first current line. The second excitation coil 63 is disposed on the outer or rear side of the first leg portion 65 of the iron core 64, and constitutes a second current line. The first current line 62 and the second current line 63 constituted by the two excitation coils are opposite in current flow direction, that is, a current flows therein counterclockwise and clockwise, respectively. The first excitation coil 62 and the second excitation coil 63 are thin with a single electric wire layer. The first excitation coil 62 on the inner side of the iron core 64 is on the side of the first leg portion 65 of the iron core 64, and in contact with an inner surface of the first leg portion 65 and separated from an inner surface of the second leg portion 66. The second excitation coil 63 on the outer side of the iron core 64 is in contact with an outer surface of the first leg portion 65.

Around the first current line 62 on the inner side of the iron core 64 is formed a magnetic circuit passing through the first leg portion 65, the beam portion 67, and the second leg portion 66, and a circumferential wall of the circular tube 50. Around the second current line 63 on the outer side of the iron core 64 is formed a magnetic circuit passing through the first leg portion 65 and the beam portion 67.

The receiving device 71 includes a coil 72 and an iron core 73. The coil 72 is a receiving coil with a plurality of turns formed in a cylindrical shape. The iron core 73 is a ferrite core, an iron core of soft magnetic material. The iron core 73 has a bar-like shape, and is concentrically fitted in the receiving coil 72. The receiving device 71 is buried in the casing 51 on a side opposite to the second current line 63 on the outer side of the iron core 64, that is, at a front side, and is disposed along approximately a radial direction in a corner between the second leg portion 66 of the iron core 64 and the sensing surface 52, with an end thereof in the vicinity of the sensing surface 52. As shown in FIG. 24, the receiving coil 72 with the iron core 73 is disposed with its axis slightly tilted from a radial direction, which is parallel to the second leg portion 66 of the iron core 64, to a side away from the second leg portion 66, that is, to the front side, such that a coil surface at an axial central position is parallel to a direction of a magnetic flux of a primary magnetic field. Namely, the receiving coil 72 is placed in a primary-magnetic-field non-sensitive position. The receiving device 71 is not in contact with the exciting device 61, and is separated therefrom.

As shown in FIG. 25, a plurality of the receiving devices 71 are radially arranged along the annular second leg portion 66 and equiangularly spaced from one another. This makes large the number of places where flaw detection is made.

When flaw detection is made on the circular tube 50 using the eddy-current flaw detection apparatus of this embodiment, the casing 51 in which the exciting device 61 and the receiving devices 71 are disposed is concentrically inserted in the circular tube 50 such that the sensing surface 52 is contacted with, or located in the vicinity of, a flaw detected surface of an inner surface of the circular tube 50. To the exciting device 61 is applied an alternating voltage. Then, an eddy current flows in the circular tube 50. Each of the receiving devices 71 substantially does not detect the state of the primary magnetic fields generated by the excitation coils 62, 63, but detects the state of a secondary magnetic field generated by the eddy current. The casing 51 located in the circular tube 50 is advanced inside the circular tube 50. When a flaw is present in the circular tube 50, the detected voltage value of a receiving device 71 that is located in the vicinity of the flaw noticeably changes.

Figure 26:
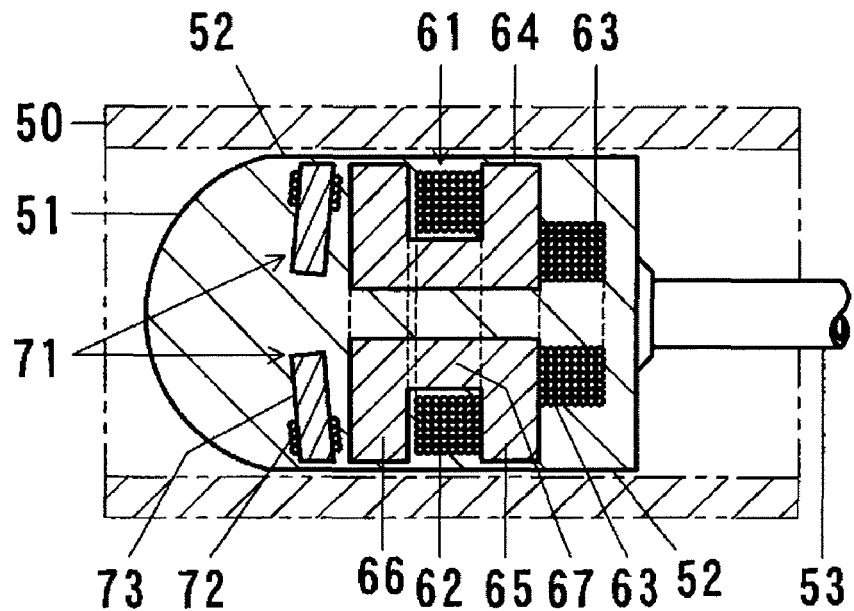
FIG. 26 A sectional side view of an eddy-current flaw detection apparatus of the tube internal fitting method according to a fifth embodiment.

Fifth Embodiment (See FIG. 26)

A fifth embodiment is slightly modified from the fourth embodiment. In an eddy-current flaw detection apparatus of the tube internal fitting method according to the present embodiment, the number of electric wire turns of the first excitation coil 62 and the second excitation coil 63 is increased, and a surface including the first current line and the second current line is tilted.

As shown in FIG. 26, the thickness of each of the first excitation coil 62 and the second excitation coil 63 is increased by multiplying their electric wire layer. The first excitation coil 62 on the inner side of the iron core 64 substantially fills up a space on the inner side of the first leg portion 65 and the second leg portion 66 of the iron core 64. The second excitation coil 63 on the outer side of the iron core 64 has a diameter smaller than that of the first excitation coil 62 on the inner side of the iron core 64, and is disposed at a radially inner side of the casing 51 or on the side of the beam portion 67 of the iron core 64, and beside the beam portion 67. A surface including the first excitation coil 62, which constitutes a first current line, and the second excitation coil 63, which constitutes a second current line, is tilted relative to the sensing surface 52.

In the other parts, the fifth embodiment is identical with the fourth embodiment. In the drawing, the same reference numerals are used as in the fourth embodiment.

Modification

The fourth and fifth embodiments are for detecting a flaw in a circular tube 50, and the casing 51 in which the exciting device 61 and the receiving devices 71 are disposed is circular in cross section, and the exciting device 61 is annular. For detecting a flaw in a rectangular tube, a casing in which an exciting device and receiving devices are disposed is formed in a rectangular shape in cross section such that the casing is fitted in the rectangular tube, the exciting device is formed in a rectangular annular shape, and the receiving devices are arranged along a second leg portion of the rectangular annular shape and are spaced from one another.

Figure 27:
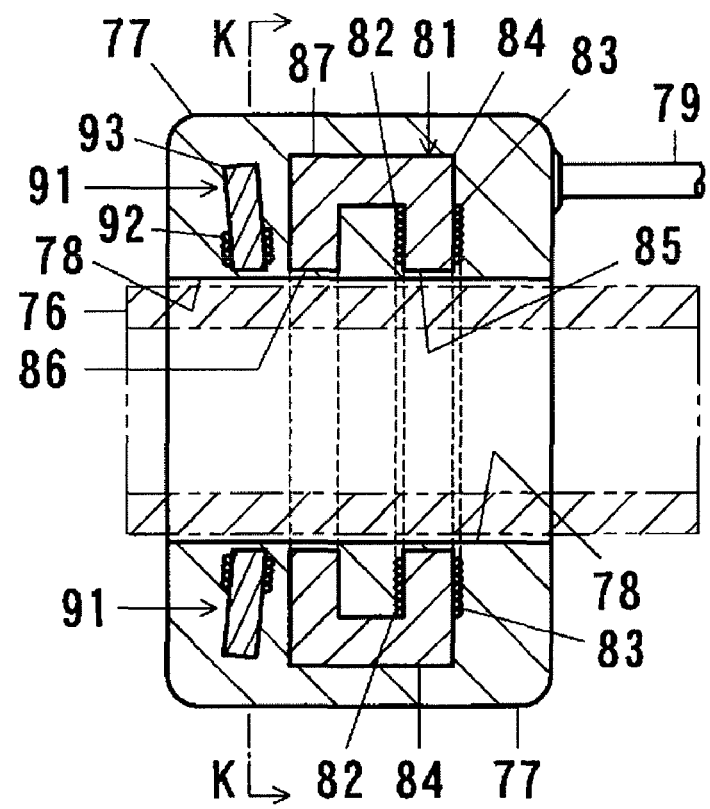
FIG. 27 A sectional side view of an eddy-current flaw detection apparatus of a tube external fitting method according to a sixth embodiment.
Figure 28:
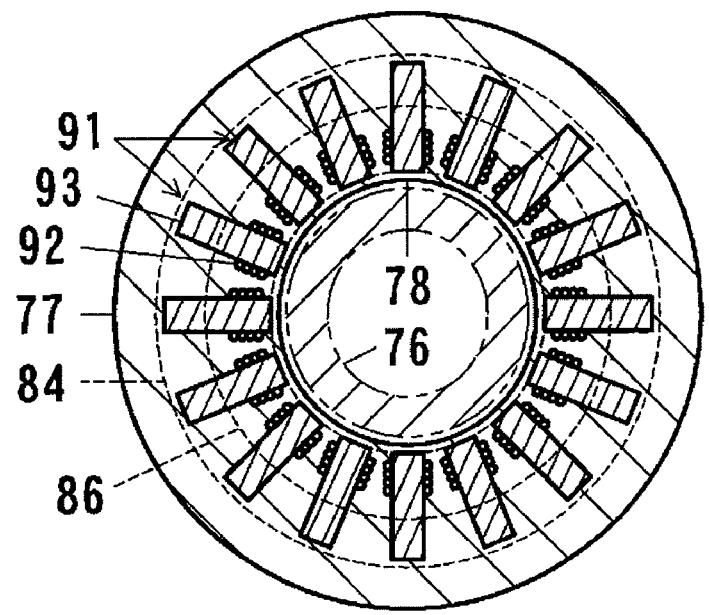
FIG. 28 A cross-sectional view taken along a line K-K in FIG. 27.

Sixth Embodiment (See FIGS. 27 and 28)

A sixth embodiment is for detecting a flaw in a circular tube 76 as a non-magnetic metal tube, and uses a tube external fitting method.

As shown in FIGS. 27 and 28, an eddy-current flaw detection apparatus for circular tube according to the present embodiment has a casing 77 in which an exciting device 81 and receiving devices 91 are disposed. The casing 77 is a non-magnetic insulator formed of synthetic resin. The casing 77 has an annular shape such that the casing 77 is concentrically fitted on an outer side of the circular tube 76, and its inner circumferential surface 78 which is a cylindrical surface defining a bore functions as a sensing surface to be contacted with or located in the vicinity of an outer cylindrical surface of the circular tube 76 as a flaw detected surface. At a rear surface of the casing 77 is connected a cable 79 through which conducting wires of the exciting device 81 and the receiving device 91 extend to the external. The exciting device 81 and the receiving devices 91 are connected to an exciting circuit and a receiving circuit (neither shown), respectively, via the cable 79.

The exciting device 81 includes coils 82, 83 and an iron core 84. The iron core 84 is a ferrite core, an iron core of soft magnetic material. The iron core 84 is annular, and has a groove concentrically formed on an inner circumferential surface thereof, and is gate-shaped in cross section. The iron core 84 has a first leg portion 85 and a second leg portion 86 located on opposite sides of the groove, and a beam portion 87 connecting ends of the leg portions 85, 86 on a radially outer side. The coils 82, 83 are excitation coils with a plurality of turns, and are two separate coils, namely, a first excitation coil 82 and a second excitation coil 83. The two excitation coils 82, 83 are annular and have identical dimensions.

The annular iron core 84 is concentrically buried in the casing 77, and disposed such that an opening of the groove on a side opposite to the beam portion 87, that is, on a radially inner side, faces the sensing surface 78 and ends of the two leg portions 85, 86 are in the vicinity of the sensing surface 78. The two leg portions 85, 86 are perpendicular to the sensing surface 78. The two annular excitation coils 82, 83 are concentrically buried in the casing 77 and arranged in a front-rear direction. The first excitation coil 82 is disposed in the groove on the inner side of the two leg portions 85, 86 of the iron core 84, and constitutes a first current line. The second excitation coil 83 is disposed on the outer or rear side of the first leg portion 85 of the iron core 84, and constitutes a second current line. The first current line 82 and the second current line 83 constituted by the two excitation coils are opposite in current flow direction, that is, a current flows therein counterclockwise and clockwise, respectively. The first excitation coil 82 and the second excitation coil 83 are thin with a single electric wire layer. The first excitation coil 82 on the inner side of the iron core 84 is on the side of the first leg portion 85 of the iron core 84, and in contact with an inner surface of the first leg portion 85 and separated from an inner surface of the second leg portion 86. The second excitation coil 83 on the outer side of the iron core 84 is in contact with an outer surface of the first leg portion 85.

Around the first current line 82 on the inner side of the iron core 84 is formed a magnetic circuit passing through the first leg portion 85, the beam portion 87, and the second leg portion 86, and a circumferential wall of the circular tube 76. Around the second current line 83 on the outer side of the iron core 84 is formed a magnetic circuit passing through the first leg portion 85 and the beam portion 87.

The receiving device 91 includes a coil 92 and an iron core 93. The coil 92 is a receiving coil with a plurality of turns formed in a cylindrical shape. The iron core 93 is a ferrite core, an iron core of soft magnetic material. The iron core 93 has a bar-like shape, and is concentrically fitted in the receiving coil 92. The receiving device 91 is buried in the casing 77 on a side opposite to the second current line 83 on the outer side of the iron core 84, that is, at a front side, and is disposed along approximately a radial direction in a corner between the second leg portion 86 of the iron core 84 and the sensing surface 78, with an end thereof in the vicinity of the sensing surface 78. As shown in FIG. 27, the receiving coil 92 with the iron core 93 is disposed with its axis slightly tilted from a radial direction, which is parallel to the second leg portion 86 of the iron core 84, to a side away from the second leg portion 86, that is, to the front side, such that a coil surface at an axial central position is parallel to a direction of a magnetic flux of a primary magnetic field. The receiving coil 92 is placed in a primary-magnetic-field non-sensitive position. The receiving device 91 is not in contact with the exciting device 81, and is separated therefrom.

As shown in FIG. 28, a plurality of the receiving devices 91 are radially arranged along the annular second leg portion 86 and equiangularly spaced from one another. This makes large the number of places where flaw detection is made.

When flaw detection is made on the circular tube 76 using the eddy-current flaw detection apparatus of this embodiment, the casing 77 in which the exciting device 81 and the receiving devices 91 are disposed is concentrically fitted on an outer side of the circular tube 76 such that the sensing surface 78 is contacted with or located in the vicinity of a flaw detected surface of an outer surface of the circular tube 76. To the exciting device 81 is applied an alternating voltage. Then, an eddy current flows in the circular tube 76. Each of the receiving devices 91 substantially does not detect the state of the primary magnetic fields generated by the excitation coils 82, 83, but detects the state of a secondary magnetic field generated by the eddy current. The casing 77 located on the outer side of the circular tube 76 is advanced along the circular tube 76. When a flaw is present in the circular tube 76, the detected voltage value of a receiving device 91 that is located in the vicinity of the flaw noticeably changes.

Figure 29:
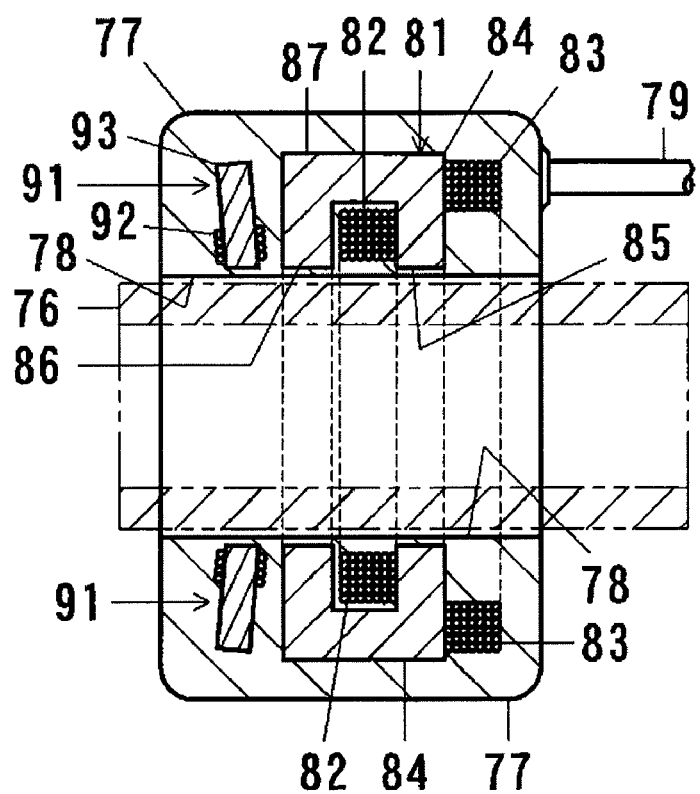
FIG. 29 A sectional side view of an eddy-current flaw detection apparatus of the tube external fitting method according to a seventh embodiment.

Seventh Embodiment (See FIG. 29)

A seventh embodiment is slightly modified from the sixth embodiment. In an eddy-current flaw detection apparatus of the tube external fitting method according to the present embodiment, the number of electric wire turns of each of the first excitation coil 82 and the second excitation coil 83 is increased, and a surface including the first current line and the second current line is tilted.

As shown in FIG. 29, the thickness of each of the first excitation coil 82 and the second excitation coil 83 is increased by multiplying their electric wire layer. The first excitation coil 82 on the inner side of the iron core 84 substantially fills up a space on the inner side of the first leg portion 85 and the second leg portion 86 of the iron core 84. The second excitation coil 83 on the outer side of the iron core 84 has a diameter larger than that of the first excitation coil 82 on the inner side of the iron core 84, and is disposed at a radially outer side of the casing 77 or on the side of the beam portion 87 of the iron core 84, and beside the beam portion 87. A surface including the first excitation coil 82, which constitutes a first current line, and the second excitation coil 83, which constitutes a second current line, is tilted relative to the sensing surface 78.

In the other parts, the seventh embodiment is identical with the sixth embodiment. In the drawing, the same reference numerals are used as in the sixth embodiment.

Modifications (1) The sixth and seventh embodiments are for detecting a flaw in a circular tube 76, and the annular casing 77 in which the exciting device 81 and the receiving devices 91 are disposed is such that its bore is circular in cross section. The exciting device 81 is annular. For detecting a flaw in a rectangular tube or a rectangular bar, the annular casing in which the exciting device and the receiving devices are disposed is formed such that its bore has a rectangular shape in cross section to make the casing fit on an outer side of the rectangular tube or the rectangular bar, the exciting device is formed in a rectangular annular shape, and the receiving devices are arranged along a second leg portion of the rectangular annular shape and are spaced from one another.

(2) In the sixth and seventh embodiments, the iron core 84 gate-shaped in cross section is constituted by a single annular member. It may be constituted by a plurality of segments circularly arranged.

INDUSTRIAL APPLICABILITY

The invention is applicable to a flaw detection on a plate, a tube, or a bar, which is made of a conductor such as metal and constitutes equipment in a factory or an electric power plant.

The invention claimed is:

1. A method of eddy-current flaw detection in which an exciting device and a receiving device are disposed in the vicinity of a conductor, which is a subject of the flaw detection, and an eddy current is generated in the conductor by a primary magnetic field generated by the exciting device to generate a secondary magnetic field, the state of the magnetic field is detected by the receiving device to detect the flaw based on a detection signal of the receiving device, wherein the exciting device includes an excitation coil and an iron core, the excitation coil having a first current line and a second current line in which an electric current flows in opposite directions, the iron core being gate-shaped in cross section and having a first leg portion, a second leg portion, and a beam portion connecting the two leg portions, an opening of the iron core on a side opposite to the beam portion facing the conductor, the first current line being disposed on an inner side of the first leg portion and the second leg portion of the iron core, and the second current line being disposed on an outer side of the first leg portion of the iron core, a magnetic circuit is formed around the first current line on the inner side of the iron core and passes through the first leg portion, the beam portion, and the second leg portion of the iron core, and the conductor, and a magnetic circuit is formed around the second current line on the outer side of the iron core and passes through the first leg portion and the beam portion of the iron core, and the receiving device is disposed in a corner between the second leg portion of the iron core and the conductor, on a side opposite to the second current line on the outer side of the iron core.

2. A method according to claim 1, wherein the receiving device is disposed at a position substantially not to detect the state of a primary magnetic field generated by the first current line on the inner side of the iron core, and detects the state of the secondary magnetic field.

3. An apparatus of eddy-current flaw detection in which an exciting device and a receiving device are disposed in the vicinity of a conductor, which is a subject of the flaw detection, and an eddy current is generated in the conductor by a primary magnetic field generated by the exciting device to generate a secondary magnetic field, the state of the magnetic field is detected by the receiving device to detect the flaw based on a detection signal of the receiving device, wherein the exciting device and the receiving device are disposed in a casing that is a non-magnetic insulator, the casing includes a sensing surface, which is contacted with or held in the vicinity of a flaw detected surface of the conductor, the exciting device includes an excitation coil and an iron core, the excitation coil having a first current line and a second current line in which an electric current flows in opposite directions, the iron core being gate-shaped in cross section and having a first leg portion, a second leg portion, and a beam portion connecting the two leg portions, an opening of the iron core on a side opposite to the beam portion facing the sensing surface, ends of the two leg portions being disposed in the vicinity of the sensing surface, the first current line being disposed on an inner side of the first leg portion and the second leg portion of the iron core, and the second current line being disposed on an outer side of the first leg portion of the iron core, and the receiving device is disposed in a corner between the second leg portion of the iron core and the sensing surface, on a side opposite to the second current line on the outer side of the iron core, with an end of the receiving device being disposed in the vicinity of the sensing surface.

4. An apparatus according to claim 3, wherein the iron core of the exciting device has an elongate shape long in a direction of a normal to the gate-shaped cross section, and the excitation coil of the exciting device has an elongate frame-like shape and is fitted on the first leg portion of the iron core, and a plurality of the receiving devices are arranged along a longitudinal direction of the exciting device and spaced from one another.

5. An apparatus according to claim 3, wherein a plurality of the iron cores of the exciting device are arranged along a direction of a normal to the gate-shaped cross section of the iron cores and spaced from one another, the excitation coil of the exciting device has an elongate frame-like shape and is fitted on the first leg portions of the plurality of the iron cores, and the receiving device is disposed on an outer side of the second leg portion of each of the iron cores of the exciting device, each of the iron cores of the exciting device is paired with the receiving device disposed on the outer side of the second leg portion of the iron core, and the pairs of the iron cores and the receiving devices are arranged along the direction of the normal to the gate-shaped cross section of the iron cores, and the casing and the excitation coil are bendable between each two adjacent pairs of the iron cores and the receiving devices, and the casing in which the exciting device and the receiving devices are disposed is bendable such that a shape thereof in the direction of the normal to the gate-shaped cross section of the iron cores conforms to a curve of the flaw detected surface of the conductor.

6. An apparatus according to claim 3, wherein the casing is shaped to be fitted in a tube as the conductor, and the sensing surface of the casing is provided by an outer circumferential surface of the casing, which faces an inner circumferential surface of the tube, the iron core of the exciting device has an annular shape with a groove formed on an outer circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

7. An apparatus according to claim 3, wherein the casing is shaped to be fitted on an outer side of a tube or a bar as the conductor, and the sensing surface of the casing is provided by an inner circumferential surface of the casing, which faces an outer circumferential surface of the tube or the bar, the iron core of the exciting device has an annular shape with a groove formed on an inner circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

8. An apparatus according to claim 3, wherein the first current line on the inner side of the iron core substantially fills up an inner space of the iron core, and the second current line on the outer side of the iron core is disposed beside the beam portion of the iron core.

9. An apparatus according to claim 8, wherein the receiving device is disposed at a position substantially not to detect the state of a primary magnetic field generated by the first current line on the inner side of the iron core.

10. An apparatus according to claim 8, wherein the iron core of the exciting device has an elongate shape long in a direction of a normal to the gate-shaped cross section, and the excitation coil of the exciting device has an elongate frame-like shape and is fitted on the first leg portion of the iron core, and a plurality of the receiving devices are arranged along a longitudinal direction of the exciting device and spaced from one another.

11. An apparatus according to claim 8, wherein a plurality of the iron cores of the exciting device are arranged along a direction of a normal to the gate-shaped cross section of the iron cores and spaced from one another, the excitation coil of the exciting device has an elongate frame-like shape and is fitted on the first leg portions of the plurality of the iron cores, and the receiving device is disposed on an outer side of the second leg portion of each of the iron cores of the exciting device, each of the iron cores of the exciting device is paired with the receiving device disposed on the outer side of the second leg portion of the iron core, and the pairs of the iron cores and the receiving devices are arranged along the direction of the normal to the gate-shaped cross section of the iron cores, and the casing and the excitation coil are bendable between each two adjacent pairs of the iron cores and the receiving devices, and the casing in which the exciting device and the receiving devices are disposed is bendable such that a shape thereof in the direction of the normal to the gate-shaped cross section of the iron cores conforms to a curve of the flaw detected surface of the conductor.

12. An apparatus according to claim 8, wherein the casing is shaped to be fitted in a tube as the conductor, and the sensing surface of the casing is provided by an outer circumferential surface of the casing, which faces an inner circumferential surface of the tube, the iron core of the exciting device has an annular shape with a groove formed on an outer circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

13. An apparatus according to claim 8, wherein the casing is shaped to be fitted on an outer side of a tube or a bar as the conductor, and the sensing surface of the casing is provided by an inner circumferential surface of the casing, which faces an outer circumferential surface of the tube or the bar, the iron core of the exciting device has an annular shape with a groove formed on an inner circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

14. An apparatus according to claim 3, wherein the receiving device is disposed at a position substantially not to detect the state of a primary magnetic field generated by the first current line on the inner side of the iron core.

15. An apparatus according to claim 14, wherein the iron core of the exciting device has an elongate shape long in a direction of a normal to the gate-shaped cross section, and the excitation coil of the exciting device has an elongate frame-like shape and is fitted on the first leg portion of the iron core, and a plurality of the receiving devices are arranged along a longitudinal direction of the exciting device and spaced from one another.

16. An apparatus according to claim 14, wherein a plurality of the iron cores of the exciting device are arranged along a direction of a normal to the gate-shaped cross section of the iron cores and spaced from one another, the excitation coil of the exciting device has an elongate frame-like shape and is fitted on the first leg portions of the plurality of the iron cores, and the receiving device is disposed on an outer side of the second leg portion of each of the iron cores of the exciting device, each of the iron cores of the exciting device is paired with the receiving device disposed on the outer side of the second leg portion of the iron core, and the pairs of the iron cores and the receiving devices are arranged along the direction of the normal to the gate-shaped cross section of the iron cores, and the casing and the excitation coil are bendable between each two adjacent pairs of the iron cores and the receiving devices, and the casing in which the exciting device and the receiving devices are disposed is bendable such that a shape thereof in the direction of the normal to the gate-shaped cross section of the iron cores conforms to a curve of the flaw detected surface of the conductor.

17. An apparatus according to claim 14, wherein the casing is shaped to be fitted in a tube as the conductor, and the sensing surface of the casing is provided by an outer circumferential surface of the casing, which faces an inner circumferential surface of the tube, the iron core of the exciting device has an annular shape with a groove formed on an outer circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

18. An apparatus according to claim 14, wherein the casing is shaped to be fitted on an outer side of a tube or a bar as the conductor, and the sensing surface of the casing is provided by an inner circumferential surface of the casing, which faces an outer circumferential surface of the tube or the bar, the iron core of the exciting device has an annular shape with a groove formed on an inner circumferential surface thereof and is gate-shaped in cross section, and the excitation coil of the exciting device is annular and is provided by a first excitation coil and a second excitation coil respectively constituting the first current line and the second current line, the first excitation coil being disposed in the groove on the inner side of the first leg portion and the second leg portion of the iron core, and the second excitation coil being disposed on the outer side of the first leg portion of the iron core, and a plurality of the receiving devices are arranged along the second leg portion of the annular iron core and spaced from one another.

* * * * *